United States Patent
Watterson et al.

(10) Patent No.: US 10,023,534 B2
(45) Date of Patent: Jul. 17, 2018

(54) CARBAZOLE AND TETRAHYDROCARBAZOLE COMPOUNDS USEFUL AS INHIBITORS OF BTK

(71) Applicant: BRISTOL-MYERS SQUIBB COMPANY, Princeton, NJ (US)

(72) Inventors: Scott Hunter Watterson, Pennington, NJ (US); Andrew J. Tebben, New Hope, PA (US); Saleem Ahmad, Wall, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/521,201

(22) PCT Filed: Oct. 23, 2015

(86) PCT No.: PCT/US2015/057046
§ 371 (c)(1),
(2) Date: Apr. 21, 2017

(87) PCT Pub. No.: WO2016/065222
PCT Pub. Date: Apr. 28, 2016

(65) Prior Publication Data
US 2017/0355673 A1    Dec. 14, 2017

Related U.S. Application Data

(60) Provisional application No. 62/068,244, filed on Oct. 24, 2014.

(51) Int. Cl.
| | | |
|---|---|---|
| *A61K 31/403* | (2006.01) | |
| *A61K 31/4353* | (2006.01) | |
| *C07D 209/82* | (2006.01) | |
| *C07D 471/04* | (2006.01) | |
| *C07D 209/58* | (2006.01) | |
| *C07D 401/02* | (2006.01) | |
| *C07D 519/00* | (2006.01) | |
| *A61K 31/407* | (2006.01) | |

(Continued)

(52) U.S. Cl.
CPC .......... *C07D 209/58* (2013.01); *A61K 31/407* (2013.01); *A61K 31/4035* (2013.01); *A61K 31/437* (2013.01); *C07D 401/02* (2013.01); *C07D 471/04* (2013.01); *C07D 519/00* (2013.01)

(58) Field of Classification Search
CPC .............. A61K 31/403; A61K 31/4353; C07D 209/82; C07D 471/04
USPC ................... 514/183, 292; 546/84; 548/439
See application file for complete search history.

(56) References Cited

U.S. PATENT DOCUMENTS

| | | |
|---|---|---|
| 5,604,236 A | 2/1997 | Jakubowski et al. |
| 7,723,336 B2 | 5/2010 | Vaccaro et al. |

(Continued)

FOREIGN PATENT DOCUMENTS

| | | |
|---|---|---|
| CN | 101475571 | 7/2009 |
| WO | WO 2005/005429 | 1/2005 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
International Preliminary Report on Patentability PCT/US2015/057046, dated Apr. 25, 2017.
Kalgutkar, Amit S., et al., "Drug Discover for a New Generation of Covalent Drugs", Expert Opinion Drug Discov., vol. 7(7), (2012) pp. 561-581.

(Continued)

*Primary Examiner* — Douglas M Willis
(74) *Attorney, Agent, or Firm* — Gary Greenblatt

(57) ABSTRACT

Disclosed are compounds of Formula (I): or a salt thereof, wherein Q is: or; and X, $R_{1a}$, $R_{1b}$, $R_3$, $R_4$, and $R_5$ are defined herein. Also disclosed are methods of using such compounds as inhibitors of Bruton's tyrosine kinase (Btk), and pharmaceutical compositions comprising such compounds. These compounds are useful in treating, preventing, or slowing the progression of diseases or disorders in a variety of therapeutic areas, such as autoimmune diseases and vascular disease.

13 Claims, 1 Drawing Sheet

(51) Int. Cl.
*A61K 31/4035* (2006.01)
*A61K 31/437* (2006.01)

(56) References Cited

U.S. PATENT DOCUMENTS

| | | | |
|---|---|---|---|
| 8,084,620 | B2 | 12/2011 | Liu et al. |
| 8,362,065 | B2 | 1/2013 | Liu et al. |
| 8,685,969 | B2 | 4/2014 | Liu et al. |
| 9,334,290 | B2 | 5/2016 | Batt et al. |
| 9,688,629 | B2 | 6/2017 | Liu et al. |
| 2006/0084650 | A1 | 4/2006 | Dong et al. |
| 2008/0045536 | A1 | 2/2008 | Vaccaro et al. |
| 2009/0281131 | A1 | 11/2009 | Gopalan et al. |
| 2012/0136023 | A1 | 5/2012 | Bell et al. |
| 2016/0200710 | A1 | 7/2016 | Ko et al. |

FOREIGN PATENT DOCUMENTS

| | | |
|---|---|---|
| WO | WO 2005/014599 | 2/2005 |
| WO | WO 2005/047290 | 5/2005 |
| WO | WO 2006/053121 | 5/2006 |
| WO | WO 2006/064355 | 6/2006 |
| WO | WO 2007/061764 | 5/2007 |
| WO | WO 2008/032171 | 3/2008 |
| WO | WO 2008/033858 | 3/2008 |
| WO | WO 2009/024819 | 2/2009 |
| WO | WO 2009/075830 | 6/2009 |
| WO | WO 2009/102498 | 8/2009 |
| WO | WO 2009/141627 | 11/2009 |
| WO | WO 2010/015636 | 2/2010 |
| WO | WO 2012/059232 | 5/2012 |
| WO | WO 2012/156334 | 11/2012 |
| WO | WO 2014/064131 | 5/2014 |
| WO | WO 16/065222 | * 4/2016 |

OTHER PUBLICATIONS

Lou, Yan, et al., "Bruton's Tyrosine Kinase Inhibitors: Approaches to Potent and Selective Inhibition, Preclinical and Clinical Evaluation for Inflammatory Diseases and B Cell Malignancies", J. Med. Chem, vol. 55, (2012) pp. 4539-4550.

Barf, T. et al., "Irreversible Protein Kinase Inhibitors: Balancing the Benefits and Risks," Journal of Medicinal Chemistry, vol. 55, (2012) pp. 6243-6262.

Liu, Qingsong, et al., "Developing Irreversible Inhibitors for the Protein Kinase Cysteinome," Chemistry & Biology, vol. 20, (2013) pp. 146-159.

D'Cruz, Osmond J., et al., "Novel Bruton's Tyrosine Kinase Inhibitors Currently in Development", OncoTargets and Therapy, vol. 6, (2013) pp. 161-176.

Whang, Jennifer A., et al., "Bruton's tyrosine kinase inhibitors for the treatment of rheumatoid arthritis," Drug Discovery Today vol. 19, No. 8 (2014) pp. 1200-1204.

Bauer, Renato A., "Covalent inhibitors in drug discovery: from accidental discoveries to avoided liabilities and designed therapies", Drug Discovery Today, vol. 20, No. 9 (2015) pp. 1061-1073.

* cited by examiner

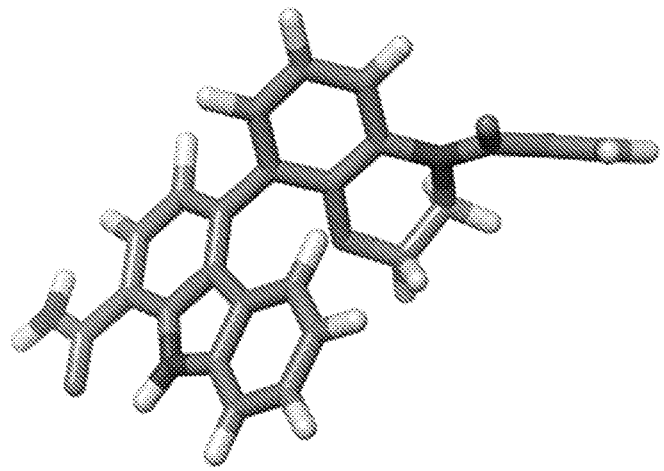

CARBAZOLE AND TETRAHYDROCARBAZOLE COMPOUNDS USEFUL AS INHIBITORS OF BTK

CROSS-REFERENCE TO RELATED APPLICATIONS

This application is a national phase application under 35 U.S.C. § 371 of International Patent Application No. PCT/US2015/057046, filed Oct. 23, 2015, which claims priority to U.S. Application Ser. No. 62/068,244, filed Oct. 24, 2014, which are expressly incorporated fully herein by reference.

DESCRIPTION

The present invention generally relates to tricyclic compounds useful as kinase inhibitors, including the modulation of Bruton's tyrosine kinase (Btk) and other Tec family kinases such as Itk. Provided herein are tricyclic compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk and other Tec family kinases such as Itk, in a mammal.

Protein kinases, the largest family of human enzymes, encompass well over 500 proteins. Btk is a member of the Tec family of tyrosine kinases, and is a regulator of early B-cell development, as well as mature B-cell activation, signaling, and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis.

A large body of evidence supports the role of B-cells and the humoral immune system in the pathogenesis of autoimmune and/or inflammatory diseases. Protein-based therapeutics such as RITUXAN®, developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

A compound that inhibits an enzyme by reacting with the enzyme to form a covalent bond can offer advantages over a compound that does not form such a covalent bond. (See, for example, Liu, Q. et al., *Chem. Biol.*, 20:146 (2013); Barf, T. et al., *J. Med. Chem.*, 55:6243 (2012); Kalgutkar, A. et al., *Expert Opin. Drug Discov.*, 7:561 (2012); and Garuti, L. et al., *Curr. Med. Chem.*, 18:2981 (2011); and references cited therein). A compound that does not form a covalent bond can dissociate from the enzyme, releasing the enzyme from the inhibition resulting from its binding. Such reversible inhibition may require a relatively high and continuous concentration of the inhibitory compound to drive the binding equilibrium toward sufficient enzyme occupancy by the inhibitor to achieve useful enzyme inhibition. A higher concentration of the compound could require administration of a higher dose of the compound to a mammal in need of such inhibition, and at a higher concentration the inhibitor could have undesired effects due to inhibition of other, non-targeted enzymes. Such off-target inhibition could include toxicity. Additionally, more frequent dosing may be required since the inhibitory compound, after dissociation from the target enzyme, can be removed from the body by metabolism and/or elimination, lowering the concentration available to achieve inhibition of the target enzyme.

In contrast, an inhibitor that forms a covalent bond with its target enzyme irreversibly inhibits the enzyme. The irreversible inhibition would result from either slow or negligible dissociation of the inhibitor, since such dissociation would require breaking a covalent bond. If the affinity of such a covalent inhibitor for its target enzyme is sufficiently great relative to affinities for other, off-target enzymes, a significantly lower concentration of the inhibitor can result in useful inhibition relative to a concentration required for reversible inhibition. The lower concentration could reduce the likelihood of undesired off-target inhibition and potential toxicity. Also, since the covalent inhibitor can bind essentially irreversibly to the target enzyme, the free (non-bound) concentration of the inhibitor can become extremely low as non-bound inhibitor is removed from the body by metabolism and/or elimination, even while useful enzyme inhibition is maintained. This can reduce the likelihood of undesired effects. Additionally, since the enzyme can be irreversibly inhibited, less frequent dosing may be required to achieve useful inhibition.

Certain reactive functional groups can be attached to a compound with good affinity for the target enzyme, which will allow formation of a covalent bond with a functional group in the target enzyme. For example, an electrophilic group such as a vinylic or acetylenic group attached to an electron-withdrawing group such as a ketone, amide, sulfone, sulfonamide, or an electron-withdrawing heterocyclic ring such as a pyridyl ring can react with a nucleophilic group present in the target enzyme, such as the thiol or thiolate group of a cysteine residue, to form a covalent bond. Such a reaction can be essentially irreversible under normal physiological conditions. In order for such a reaction to be achieved, the inhibitor compound must bind to the target enzyme and present the attached electrophilic group in a correct spatial orientation to allow favorable interaction with the attacking nucleophile. If the orientation is not correct, the covalent bond may not easily form, and the desired irreversible inhibition may not be achieved. In this case, the compound would behave like a reversible inhibitor and the benefits of irreversible inhibition may not be realized. Also, if the orientation of the electrophile on the bound inhibitor is not suitable for reaction with the nucleophilic group of the target enzyme, the inhibitor will be capable of dissociation from the target enzyme, resulting in a higher concentration of the inhibitor and a greater likelihood that the reactive electrophilic group can react with other, non-target nucleophiles and cause undesired effects such as toxicity.

U.S. Pat. Nos. 8,084,620 and 8,685,969 disclose tricyclic carboxamide compounds useful as kinase inhibitors, including the modulation of Btk and other Tec family kinases.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

There still remains a need for compounds useful as Btk inhibitors. Further, there still remains a need for compounds useful as Btk inhibitors that can be administered at lower doses or are effective at lower concentrations. Additionally, there still remains a need for compounds that have a combination of improved potency as Btk inhibitors and improved potency in the Ramos FLIPR assay.

Applicants have found potent compounds that have activity as Btk inhibitors. These compounds are provided to be useful as pharmaceuticals with desirable stability, bioavailability, therapeutic index, and toxicity values that are important to their drugability.

SUMMARY OF THE INVENTION

The present invention provides tricyclic compounds, including prodrugs thereof, which are useful as inhibitors of Btk, and are useful for the treatment of proliferative diseases, allergic diseases, autoimmune diseases and inflammatory diseases.

The present invention also provides pharmaceutical compositions comprising at least one compound of Formula (I) and a pharmaceutically acceptable carrier.

The present invention also provides a method of inhibiting Btk activity comprising administering to a mammal in need thereof at least one compound of Formula (I).

The present invention also provides a method for treating allergic disorders and/or autoimmune and/or inflammatory diseases, comprising administering to a mammal in need thereof at least one compound of Formula (I).

The present invention also provides a method for treating proliferative diseases, such as cancer, comprising administering to a mammal in need thereof at least one compound of Formula (I).

The present invention also provides a method of treating a disease or disorder associated with Btk activity, the method comprising administering to a mammal in need thereof, at least one compound of Formula (I).

The present invention also provides processes and intermediates for making the compounds of Formula (I).

The present invention also provides a compound of Formula (I) for use in therapy.

The present invention also provides the use of the compounds of Formula (I) for the manufacture of a medicament for the treatment or prophylaxis of Btk related conditions, such as proliferative diseases, allergic diseases, autoimmune diseases and inflammatory diseases.

The present invention also provides the use of the compounds of Formula (I) for the manufacture of a medicament for treatment of cancer.

The compounds of Formula (I) and compositions comprising the compounds of Formula (I) may be used in treating, preventing, or curing various Btk related conditions. Pharmaceutical compositions comprising these compounds are useful in treating, preventing, or slowing the progression of diseases or disorders in a variety of therapeutic areas, such as proliferative diseases, allergic diseases, autoimmune diseases and inflammatory diseases.

These and other features of the invention will be set forth in expanded form as the disclosure continues.

BRIEF DESCRIPTION OF THE DRAWINGS

The invention is illustrated by reference to the accompanying drawings described below.

FIG. 1 shows the absolute stereochemistry of Example 5 (left), Example 12 (center), and Example 8 (right).

DETAILED DESCRIPTION

The first aspect of the present invention provides a compound of Formula (I)

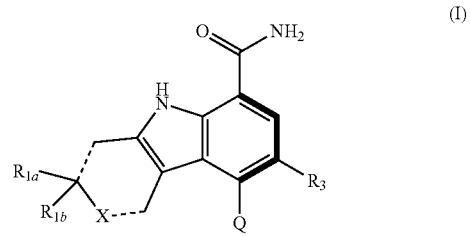

or a salt thereof, wherein:

the two dotted lines represent either two single or two double bonds; and $R_{1b}$ is present only if said two dotted lines are two single bonds;

X is:

(i) $CR_{2a}R_{2b}$ or $NR_{2b}$ when the two dotted lines represent two single bonds; or (ii) $CR_{2a}$ or N when the two dotted lines represent two double bonds;

Q is:

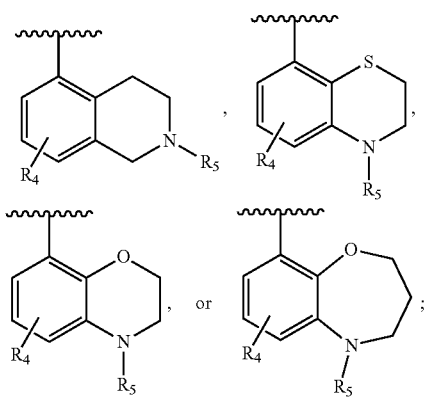

$R_{1a}$ is H, —CN, —CF$_3$, —CH$_3$, —CR$_{6a}$R$_{6b}$OH, —CH$_2$CH$_2$OH, —CH(OH)CH$_2$OH, —CH$_2$CH$_2$F, —NHR$_7$, or —C(O)NR$_{8a}$R$_{8b}$;

$R_{1b}$, when present, is H or —CH$_3$, provided that if $R_{1a}$ is H then $R_{1b}$ is also H;

$R_{2a}$ is H, F, or Cl, provided that if $R_{1a}$ is other than H then $R_{2a}$ is H;

$R_{2b}$, when present, is the same as $R_{2a}$;

$R_3$ is F, Cl, —CN, or —CH$_3$;

$R_4$ is H, F, Cl, —OCH$_3$, or —OCF$_3$;

$R_5$ is —CN or —C(O)CH═CH$_2$;

$R_{6a}$ and $R_{6b}$ are independently H or —CH$_3$;

$R_7$ is C$_{1-4}$ alkyl; and $R_{8a}$ and $R_{8b}$ are independently H or —CH$_3$.

The second aspect of the present invention provides a compound of Formula (II)

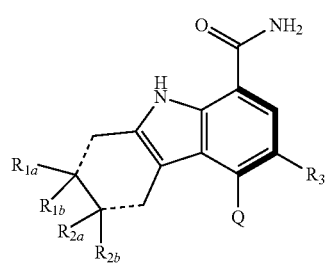

or a salt thereof, wherein:

the two dotted lines represent either two single or two double bonds; and R$_{1b}$ and R$_{2b}$ are present only if said two dotted lines are two single bonds;

Q is:

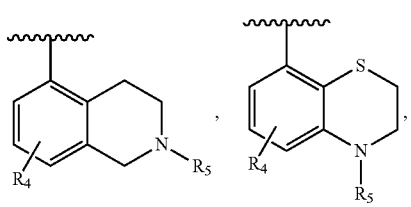

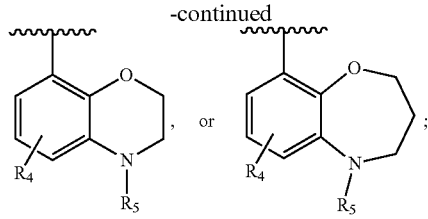

$R_{1a}$ is H, —CN, —CF$_3$, —CH$_3$, —CR$_{6a}$R$_{6b}$OH, —CH(OH)CH$_2$OH, —NHR$_7$, or —C(O)NR$_{8a}$R$_{8b}$;

$R_{1b}$, when present, is H or —CH$_3$, provided that if $R_{1a}$ is H then $R_{1b}$ is also H;

$R_{2a}$ is H or F, provided that if $R_{1a}$ is other than H then $R_{2a}$ is H;

$R_{2b}$, when present, is the same as $R_{2a}$;

$R_3$ is F, Cl, —CN, or —CH$_3$;

$R_4$ is H, F, Cl, —OCH$_3$, or —OCF$_3$;

$R_5$ is —C(O)CH═CH$_2$;

$R_{6a}$ and $R_{6b}$ are independently H or —CH$_3$;

$R_7$ is C$_{1-4}$ alkyl; and $R_{8a}$ and $R_{8b}$ are independently H or —CH$_3$.

One embodiment provides a compound of Formula (I) or a salt thereof, wherein the two dotted lines represent two double bonds and X is CR$_{2a}$. Compounds of this embodiment have the structure of Formula (Ia):

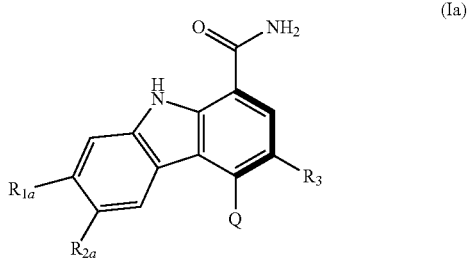

wherein Q, $R_{1a}$, $R_{2a}$, and $R_3$ are defined in the first aspect or the second aspect.

One embodiment provides a compound of Formula (I) or a salt thereof, wherein the two dotted lines represent two single bonds and X is CR$_{2a}$R$_{2b}$. Compounds of this embodiment have the structure of Formula (Ib):

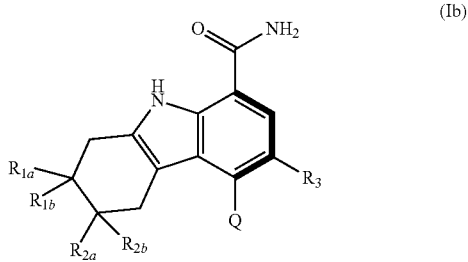

wherein Q, $R_{1a}$, $R_{1b}$, $R_{2a}$, $R_{2b}$, and $R_3$ are defined in the first aspect or the second aspect.

One embodiment provides a compound of Formula (I) or a salt thereof, wherein the two dotted lines represent two double bonds and X is N. Compounds of this embodiment have the structure of Formula (Ic):

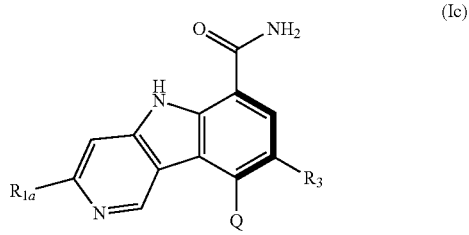

(Ic)

wherein Q, $R_{1a}$, and $R_3$ are defined in the first aspect.

One embodiment provides a compound of Formula (I) or a salt thereof, wherein the two dotted lines represent two single bonds and X is $NR_{2a}$. Compounds of this embodiment have the structure of Formula (Id):

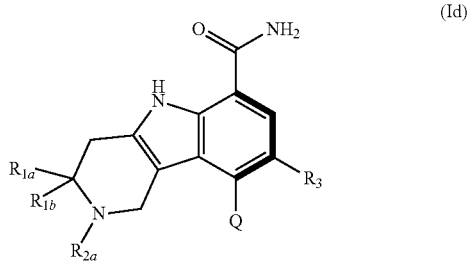

(Id)

wherein Q, $R_{1a}$, $R_{1b}$, $R_{2a}$, and $R_3$ are defined in the first aspect.

The tetrahydrocarbazole compounds represented by Formula (Ib) and the compounds represented by Formula (Id), wherein $R_{1a}$ is other than H, also have a chiral center at the carbon atom to which $R_{1a}$ is attached, and thus can exist as S- and R-isomers at this chiral center. These isomers are separable and stable. One embodiment provides such compounds of Formula (Ib) with the carbon chiral center to which $R_{1a}$ is attached as the S-isomer. One embodiment provides such compounds of Formula (Ib) with the carbon chiral center to which $R_{1a}$ is attached as the R-isomer. Another embodiment provides such compounds of Formula (Id) with the carbon chiral center at which $R_{1a}$ is attached as the S-isomer. A further embodiment provides such compounds of Formula (Id) with the carbon chiral center to which $R_{1a}$ is attached as the R-isomer.

Atropisomers are stereoisomers resulting from hindered rotation about a single bond axis where the rotational barrier is high enough to allow for the isolation of the individual rotational isomers. (LaPlante et al., *J. Med. Chem.*, 54:7005 (2011)). The compounds of Formula (I) where $R_3$ is other than hydrogen, and Q is substituted phenyl with $R_4$ other than hydrogen, substituted 1,2,3,4-tetrahydroisoquinolin-5-yl, substituted 3,4-dihydro-2H-benzo[b][1,4]oxazin-8-yl, 2,3,4,5-tetrahydro[b][1,4]oxazepin-9-yl, or substituted isoindolin-4-yl, have a stereogenic axis at the bond between the tricyclic tetrahydrocarbazole/carbazole and group Q. Due to the non-symmetric nature of the substitutions on the rings connected by this bond, and due to limited rotation about this bond caused by steric hindrance, such compounds of Formula (I) can form rotational isomers. If the rotational energy barrier is sufficiently high, hindered rotation about this bond occurs at a rate that is slow enough to allow isolation of the separated atropisomers as different compounds. Thus, these compounds of Formula (I) can form two rotational isomers which under certain circumstances, such as chromatography on a chiral stationary phase, can be separated into individual atropisomers. Such compounds of Formula (I) can be provided as a mixture of two atropisomers, or as single atropisomers. Such compounds of Formula (I) were found to be separable and stable in solution at ambient and physiological temperatures. The absolute spatial configurations of the atropisomers can be determined by single crystal x-ray crystallography. These compounds of Formula (I) can be provided as individual atropisomers or as mixtures comprising the two atropisomers of Formula (I) in any proportions.

One embodiment provides compounds of Formula (I) or a salt thereof, wherein only one atropisomer is provided, or wherein only one atropisomer mixed with a smaller amount of the other atropisomer is provided. Where the absolute configuration is not assigned, the provided atropisomer can be defined by the order of elution relative to the other atropisomer during chromatography on a chiral stationary phase under specific conditions.

The compounds of Formula (I) are atropisomers, wherein each atropisomer compound of Formula (I) can be provided substantially free of its complementary atropisomer. As used herein, "substantially free" refers to a compound of Formula (I) provided with at least 95% atropisomeric purity, preferably at least 99% atropisomeric purity, and more preferably, at least 99.5% atropisomeric purity.

One embodiment provides a compound of Formula (I), Formula (Ia), or Formula (Ib), or a salt thereof, wherein $R_{1a}$ is H, —$CF_3$, or —$C(CH_3)_2OH$; $R_{1b}$ is H; $R_{2a}$ is H or F, provided that if $R_{1a}$ is other than H then $R_{2a}$ is H; $R_{2b}$, when present, is the same as $R_{2a}$; $R_3$ is F; and $R_4$ is H; $R_5$ is —C(O)CH=$CH_2$; and Q is defined in the first aspect.

One embodiment provides a compound of Formula (I), Formula (Ia), Formula (Ib), or a salt thereof, wherein $R_{1a}$ is H, —CN, —$CF_3$, —$CR_{6a}R_{6b}OH$, or —$NHR_7$; $R_{2a}$ is H; $R_3$ is F or Cl; $R_4$ is H, F, Cl, or —$OCH_3$; $R_5$ is —C(O)CH=$CH_2$; $R_{6a}$ is H or —$CH_3$; $R_{6b}$ is H or —$CH_3$; $R_7$ is $C_{2-3}$ alkyl; and Q is defined in the first aspect.

One embodiment provides a compound of Formula (I), Formula (Ia), or Formula (Ib), or a salt thereof, wherein Q is:

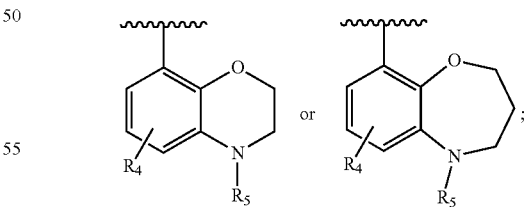

and $R_{1a}$, $R_{1b}$, $R_{2a}$, $R_{2b}$, $R_3$, $R_4$, and $R_5$ are defined in the second aspect. Included in this embodiment are compounds in which $R_{1a}$ is H or —$CF_3$ and $R_3$ is F. Also included in this embodiment are compounds of Formula (Ia) in which $R_{1a}$ is H or —$CF_3$; $R_{2a}$ is H; $R_3$ is F; and $R_4$ is H.

One embodiment provides a compound of Formula (I), Formula (Ia), or Formula (Ib), or a salt thereof, wherein Q is

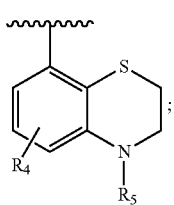

and $R_{1a}$, $R_{1b}$, $R_{2a}$, $R_{2b}$, $R_3$, $R_4$, and $R_5$ are defined in the second aspect. Included in this embodiment are compounds in which $R_{1a}$ is H or —$CF_3$ and $R_3$ is F. Also included in this embodiment are compounds of Formula (Ia) in which $R_{1a}$ is H or —$CF_3$; $R_{2a}$ is H; $R_3$ is F; and $R_4$ is H.

One embodiment provides a compound of Formula (Ib) or a salt thereof, wherein Q is

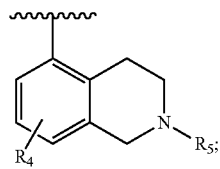

$R_{1a}$ is H, —$CH_3$, —$CF_3$, —$CR_{6a}R_{6b}OH$, or —C(O)$NR_{8a}R_{8b}$; $R_{1b}$ is H; $R_{2a}$ is H or F, provided that if $R_{1a}$ is other than H then $R_{2a}$ is H; $R_{2b}$ is H or F, provided that if $R_{2a}$ and $R_{2b}$ are the same; $R_3$ is F or Cl; $R_4$ is H, F, Cl, or —$OCH_3$; and $R_{8a}$ and $R_{8b}$ are each —$CH_3$.

One embodiment provides a compound of Formula (I), Formula (Ia), or Formula (Ib), or a salt thereof, wherein Q is

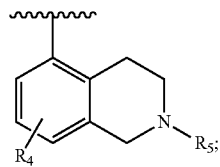

$R_{1a}$ is H, —$CF_3$, or —C($CH_3$)$_2$OH; and $R_{1b}$, $R_{2a}$, $R_{2b}$, $R_3$, $R_4$, and $R_5$ are defined in the second aspect. Also included in this embodiment are compounds in which $R_3$ is F and $R_4$ is H.

One embodiment provides a compound of Formula (I), Formula (Ic), or Formula (Id), or a salt thereof, wherein Q is

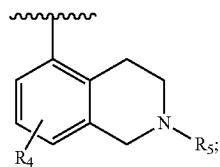

$R_{1a}$ is H, —$CF_3$, or —C($CH_3$)$_2$OH; and $R_{1b}$, $R_{2b}$, $R_3$, $R_4$, and $R_5$ are defined in the first aspect. Included in this embodiment are compounds in which $R_3$ is F or Cl; and $R_4$ is H. Also included are compounds in which $R_{2b}$ is H.

One embodiment provides a compound of Formula (I), Formula (Ia), Formula (Ib), Formula (Ic), or Formula (Id), or a salt thereof, wherein $R_3$ is F, Cl, or —CN; and $R_{1a}$, $R_{1b}$, $R_{2a}$, $R_{2b}$, $R_4$, $R_5$, and Q are defined in the first aspect. Included in this embodiment are compounds in which $R_3$ is F or —CN. Also included in this embodiment are compounds in which $R_3$ is —CN.

One embodiment provides a compound of Formula (I), Formula (Ia), Formula (Ib), Formula (Ic), or Formula (Id), or a salt thereof, wherein $R_3$ is F or Cl; and $R_{1a}$, $R_{1b}$, $R_{2a}$, $R_{2b}$, $R_4$, $R_5$, and Q are defined in the first aspect. Included in this embodiment are compounds in which $R_3$ is F. Also included in this embodiment are compounds in which $R_3$ is Cl.

One embodiment provides a compound of Formula (I), Formula (Ia), Formula (Ib), Formula (Ic), or Formula (Id), or a salt thereof, wherein $R_3$ is Cl, —CN, or —$CH_3$; and $R_{1a}$, $R_{1b}$, $R_{2a}$, $R_{2b}$, $R_4$, $R_5$, and Q are defined in the first aspect. Included in this embodiment are compounds in which $R_3$ is —CN or —$CH_3$. Also included in this embodiment are compounds in which $R_3$ is —$CH_3$.

One embodiment provides a compound of Formula (I), Formula (Ia), Formula (Ib), Formula (Ic), or Formula (Id), or a salt thereof, wherein $R_5$ is —C(O)CH=$CH_2$; and $R_{1a}$, $R_{1b}$, $R_{2a}$, $R_{2b}$, $R_3$, $R_4$, and Q are defined in the first aspect. Included in this embodiment are compounds in which $R_3$ is F or —Cl. Also included are compounds in which X is $CR_{2a}R_{2b}$ or $CR_{2a}$.

One embodiment provides a compound of Formula (I), Formula (Ia), Formula (Ib), Formula (Ic), or Formula (Id), or a salt thereof, wherein $R_5$ is —CN; and $R_{1a}$, $R_{1b}$, $R_{2a}$, $R_{2b}$, $R_3$, $R_4$, $R_5$, and Q are defined in the first aspect. Included in this embodiment are compounds in which $R_3$ is F or —Cl. Also included are compounds in which X is $CR_{2a}R_{2b}$ or $CR_{2a}$.

One embodiment provides a compound of Formula (I), Formula (Ia), Formula (Ib), Formula (Ic), or Formula (Id), or a salt thereof, wherein $R_{1a}$ is —CN, —$CF_3$, —$CH_3$, —$CR_{6a}R_{6b}OH$, —$CH_2CH_2OH$, —$CH(OH)CH_2OH$, —$CH_2CH_2F$, —$NHR_7$, or —C(O)$NR_{8a}R_{8b}$; and $R_{1b}$, $R_{2a}$, $R_{2b}$, $R_3$, $R_4$, $R_5$, $R_{6a}$, $R_{6b}$, $R_7$, $R_{8a}$, $R_{8b}$, and Q are defined in the first aspect. Included in this embodiment are compounds in which $R_{1a}$ is —CN, —$CF_3$, or —$CH_3$. Also included in this embodiment are compounds in which $R_{1a}$ is —C($CH_3$)$_2$OH, —$CH_2CH_2OH$, —$CH(OH)CH_2OH$, —$CH_2CH_2F$, or —C(O)N($CH_3$)$_2$.

One embodiment provides compounds of Formula (I) or a salt thereof, wherein said compound is (RS)-5-(2-acryloyl-1,2,3,4-tetrahydroisoquinolin-5-yl)-3,3,6-trifluoro-2,3,4,9-tetrahydro-1H-carbazole-8-carboxamide (1); (RS)-4-(2-acryloyl-1,2,3,4-tetrahydroisoquinolin-5-yl)-3-fluoro-9H-carbazole-1-carboxamide (2); (RS)-4-(4-acryloyl-3,4-dihydro-2H-benzo[b][1,4]oxazin-8-yl)-3-fluoro-9H-carbazole-1-carboxamide (3); (RS)-4-(2-acryloyl-1,2,3,4-tetrahydroisoquinolin-5-yl)-3-fluoro-7-(trifluoromethyl)-9H-carbazole-1-carboxamide (4); 4-(2-acryloyl-1,2,3,4-tetrahydroisoquinolin-5-yl)-3-fluoro-9H-carbazole-1-carboxamide, single enantiomer (5); 5-(2-acryloyl-1,2,3,4-tetrahydroisoquinolin-5-yl)-3,3,6-trifluoro-2,3,4,9-tetrahydro-1H-carbazole-8-carboxamide, single enantiomer (6); 4-(2-acryloyl-1,2,3,4-tetrahydroisoquinolin-5-yl)-3-fluoro-7-(trifluoromethyl)-9H-carbazole-1-carboxamide, single enantiomer (7); 4-(4-acryloyl-3,4-dihydro-2H-benzo[b][1,4]oxazin-8-yl)-3-fluoro-9H-carbazole-1-carboxamide, single enantiomer (8); 5-(2-acryloyl-1,2,3,4-tetrahydroisoquinolin-5-yl)-6-fluoro-2-(S)-(2-hydroxypropan-2-yl)-2,3,4,9-tetrahydro-1H-carbazole-8-carboxamide, single diastereomer (9); 5-(2-acryloyl-1,2,3,4-tetrahydroisoquinolin-5-yl)-6-fluoro-2-(trifluoromethyl)-2,3,4,9-tetrahydro-1H-carbazole-8-carboxamide, single homochiral diastereomers (10 and 11); 4-(5-acryloyl-2,3,4,5-tetrahydrobenzo[b][1,4]oxazepin-9-yl)-3-fluoro-7-(trifluoromethyl)-9H-carbazole-1-carboxamide, single enantiomeric atropisomer (12); (RS)-4-(4-acryloyl-3,4-dihydro-2H-benzo[b][1,4]thiazin-8-yl)-3-fluoro-9H-carbazole-1-carboxamide (13); 4-(4-acryloyl-3,4-dihydro-2H-benzo[b][1,4]thiazin-8-yl)-3-fluoro-9H-carbazole-1-carboxamide, single enantiomer (14); 4-(2-acryloyl-1,2,3,4-tetrahydroisoquinolin-5-yl)-3-chloro-9H-carbazole-1-carboxamide (24); 4-(2-acryloyl-1,2,3,4-tetrahydroisoquinolin-5-yl)-3-fluoro-7-(2-hydroxyethyl)-9H-carbazole-1-carboxamide, racemate (25); 4-(2-acryloyl-1,2,3,4-tetrahydroisoquinolin-5-yl)-3-fluoro-7-(2-fluoroethyl)-9H-carbazole-1-carboxamide, racemate, (26); 4-(2-cyano-1,2,3,4-tetrahydroisoquinolin-5-yl)-3-fluoro-7-(2-hydroxyethyl)-9H-carbazole-1-carboxamide, racemate (27); 4-(2-acryloyl-1,2,3,4-tetrahydroisoquinolin-5-yl)-3-fluoro-N7,N7-dimethyl-9H-carbazole-1,7-dicarboxamide, racemate (28); 4-(2-acryloyl-1,2,3,4-tetrahydroisoquinolin-5-yl)-6-chloro-3-fluoro-9H-carbazole-1-carboxamide, racemate (29); 4-(2-acryloyl-1,2,3,4-tetrahydroisoquinolin-5-yl)-3-fluoro-9H-carbazole-1-carboxamide, racemate (30); 9-(2-acryloyl-1,2,3,4-tetrahydroisoquinolin-5-yl)-8-fluoro-5H-pyrido[4,3-b]indole-6-carboxamide, racemate (31); 5-(2-acryloyl-1,2,3,4-tetrahydroisoquinolin-5-yl)-6-chloro-2,3,4,9-tetrahydro-1H-carbazole-8-carboxamide, racemate (32); or 9-(2-acryloyl-1,2,3,4-tetrahydroisoquinolin-5-yl)-8-chloro-2,3,4,5-tetrahydro-1H-pyrido[4,3-b]indole-6-carboxamide, racemate (33).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to six carbon atoms.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

Certain compounds of Formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic salts formed with inorganic and/or organic acids. Pharmaceutically acceptable (i.e., non-toxic, physiologically acceptable) salts are preferred, such as, for example, salts in which the anion does not contribute significantly to the toxicity or biological activity of the salt. However, other salts may be useful, e.g., in isolation or purification steps which may be employed during preparation, and thus, are contemplated within the scope of the invention. Salts of the compounds of the Formula (I) may be formed, for example, by reacting a compound of the Formula (I) with an amount of acid such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example, when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to Btk, or effective to treat or prevent autoimmune and/or inflammatory and/or proliferative disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers, etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of the invention modulate kinase activity, including the modulation of Btk. Other types of kinase activity that may be modulated by the compounds of the instant invention include, but are not limited to, the Tec family of kinases, such as BMX, Btk, ITK, TXK and Tec, and mutants thereof.

Accordingly, compounds of Formula (I) have utility in treating conditions associated with the modulation of kinase activity, and particularly the selective inhibition of Btk activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, Sjögren's syndrome, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, Kawasaki disease, chronic inflammatory demyelinating polyneuropathy (CIDP), dermatomyositis, uveitis, anti-factor-VIII disease, ankylosing spondylitis, myasthenia gravis, Goodpasture's disease, antiphospholipid syndrome, ANCA-associated vasculitis, dermatomyositis/polymyositis, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris.

Preferred methods of treatment are those wherein the condition is selected from Crohn's and ulcerative colitis, allograft rejection, rheumatoid arthritis, psoriasis, ankylosing spondylitis, psoriatic arthritis, pemphigus vulgaris and multiple sclerosis. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

"Therapeutically effective amount" is intended to include an amount of a compound of the present invention that is effective when administered alone or in combination to inhibit Btk.

One embodiment provides methods for treating such Btk kinase-associated conditions, comprising administering to a subject in need thereof at least one compound of Formula (I). A therapeutically-effective amount for treating such conditions may be administered. The methods of the present embodiment may be employed to treat Btk kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating Btk kinase-associated conditions may comprise administering at least one compound of Formula (I) alone or in combination with each other and/or other suitable therapeutic agents useful in treating such conditions. Therapeutically-effective amounts of at least one compound of Formula (I) and other suitable therapeutic agents for treating such conditions may be administered. Accordingly, "therapeutically effective amount" is also intended to include an amount of the combination of compounds claimed that is effective to treat Btk kinase-associated conditions. The combination of compounds is preferably a synergistic combination. Synergy, as described, for example, by Chou et al., *Adv. Enzyme Regul.*, 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-a] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (I) for use in therapy. In the present embodiment, the use in therapy may include the administration of a therapeutically-effective amount of a compound of Formula (I).

Another embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment of prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of prophylaxis of an allergic disorder and/or autoimmune and/or inflammatory disease.

The present invention further includes compositions comprising one or more compounds of Formula (I) and a pharmaceutically acceptable carrier.

The present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of compounds of Formula (I) as specified in the "Examples" section below, have been tested in one or more of the assays described below.

In one embodiment, the compounds of Formula (I) inhibit Btk enzymes with $IC_{50}$ values of 0.4 nM or less, for example, from 0.001 to 0.4 nM, as measured by the Human Recombinant Btk enzyme assay. Included in this embodiment are compounds of Formula (I) which inhibit Btk enzymes with $IC_{50}$ values of 0.3 nM and less, for example, from 0.001 to 0.3 nM. Other compounds of this embodiment inhibit Btk enzymes with $IC_{50}$ values of 0.25 nM and less, for example, from 0.001 to 0.25 nM.

In one embodiment, the compounds of Formula (I) have useful potency in the inhibition of intracellular calcium flux in Ramos RA1 B cells stimulated with anti-human IgM, with $IC_{50}$ values of 25 nM or less, for example, from 0.1 to 25 nM. Included in this embodiment are compounds of Formula (I) that have potency in the inhibition of intracellular calcium flux in Ramos RA1 B cells stimulated with anti-human IgM with $IC_{50}$ values of 20 nM or less, for example, from 0.1 to 20 nM; and with $IC_{50}$ values of 15 nM or less, for example, from 0.1 to 15 nM.

In one embodiment, the compounds of Formula (I) inhibit Btk enzymes with $IC_{50}$ values of 0.4 nM or less, for example, from 0.001 to 0.4 nM, as measured by the Human Recombinant Btk enzyme assay, and inhibit the intracellular calcium flux in Ramos RA1 B cells stimulated with anti-human IgM, with $IC_{50}$ values of 25 nM or less, for example, from 0.1 to 25 nM.

In one embodiment, the compounds of Formula (I) inhibit Btk enzymes with $IC_{50}$ values of 0.4 nM or less, for example, from 0.001 to 0.4 nM, as measured by the Human Recombinant Btk enzyme assay, and inhibit the intracellular calcium flux in Ramos RA1 B cells stimulated with anti-human IgM, with $IC_{50}$ values of 20 nM or less, for example, from 0.1 to 20 nM.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will be recognized by one skilled in the art of organic synthesis that some functional groups present in intermediate compounds, or in compounds of Formula (I), may be unstable to, or otherwise unsuited for, some of the reaction conditions used to prepare them or to convert them to other intermediates or to compounds of Formula (I). In these cases, the functional groups may be protected by conversion to alternative functional groups which are stable to, or more suited for, the reaction conditions to be employed. These protected functional group can then be converted back to the original functional group at a later stage of the synthesis. Examples are the protection of a carboxylic acid as a carboxylate ester, the protection of a primary or secondary amine as a tert-butyloxycarbonyl (Boc) derivative or benzyloxycarbonyl (Cbz) derivative, or the protection of a carbazole or tetrahydrocarbazole nitrogen as a 2-trimethylsilylethoxymethyl (SEM) derivative. The use of protecting groups is well known in the literature; an authoritative account describing the many alternatives to the trained practitioner is Wuts, P. et al., *Greene's Protective Groups in Organic Synthesis*, Fourth Edition, Wiley-Interscience (2006).

Compounds 3, representing certain compounds of Formula (I), can be prepared using methods shown in Scheme 1.

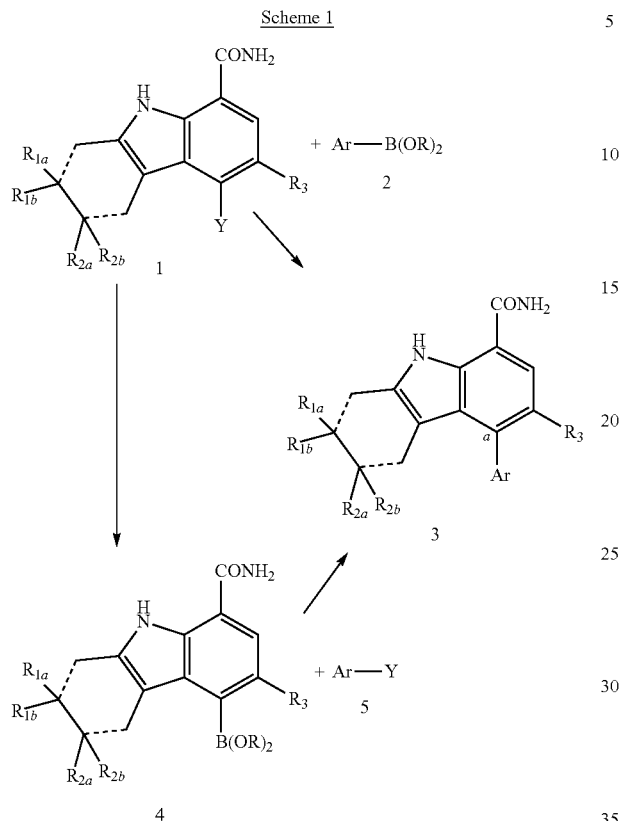

A substituted carbazolecarboxamide or tetrahydrocarbazolecarboxamide 1, where Y is an appropriate group such as Br, Cl, or trifluoromethanesulfonyloxy, can be reacted with a boronic acid or boronic acid ester 2 (where R is, for example, H, alkyl, or taken together form an optionally substituted 1,3,2-dioxaboralane or 1,3,2-dioxaborinane), where Ar represents one of the groups Q of Formula (I), to provide a compound 3. This reaction may be performed by using a suitable base such as potassium carbonate, cesium carbonate or tripotassium phosphate, and a suitable catalyst such as tetrakis(triphenylphosphine)palladium, 1,1'-bis(diphenylphosphino)ferrocene palladium(II) chloride, or 1,1'-bis(di-tert-butylphosphino)ferrocene palladium(II) chloride, in a suitable solvent such as 1,4-dioxane, N,N-dimethylformamide or tetrahydrofuran, optionally with one or more suitable cosolvents such as water or ethanol. Such coupling reactions are commonly known as Suzuki-Miyaura coupling reactions, and are known in the chemical literature (see, for example, Heravi, M. et al., Tetrahedron, 68:9145 (2012), and references cited therein).

Alternatively, a substituted carbazolecarboxamide or tetrahydrocarbazolecarboxamide 1 can be converted to the corresponding boronic acid or boronic acid ester 4 (where R is, for example, H, alkyl, or taken together form an optionally substituted 1,3,2-dioxaboralane or 1,3,2-dioxaborinane), using methods known in the chemical literature (see, for example, Ishiyama, T. et al., Tetrahedron, 57:9813 (2001), and references cited therein). Examples of such methods are the reaction of 1 with a reagent such as 4,4,4',4',5,5,5',5'-octamethyl-2,2'-bi(1,3,2-dioxaborolane) in the presence of a base such as potassium acetate and a suitable catalyst such as 1,1'-bis(diphenylphosphino)ferrocene palladium(II) chloride in a suitable solvent. Alternatively, reaction of a compound 1 where Y is Br with an organometallic reagent such as butyllithium or isopropylmagnesium chloride, followed by treatment with a boric acid ester such as trimethyl borate or tri-isopropyl borate, then followed by hydrolysis of the resulting boronic acid ester, can provide a boronic acid 4 (R=H). Reaction of a compound 4 with a suitable compound 5, wherein Ar represents one of the groups Q of Formula (I), and Y is an appropriate group such as Br, Cl, or trifluoromethanesulfonyloxy, using the Suzuki-Miyaura coupling reaction as described above, can also provide a compound 3.

A compound 2 can be prepared from a compound 5 using the same method described for the preparation of a compound 4 from a compound 1.

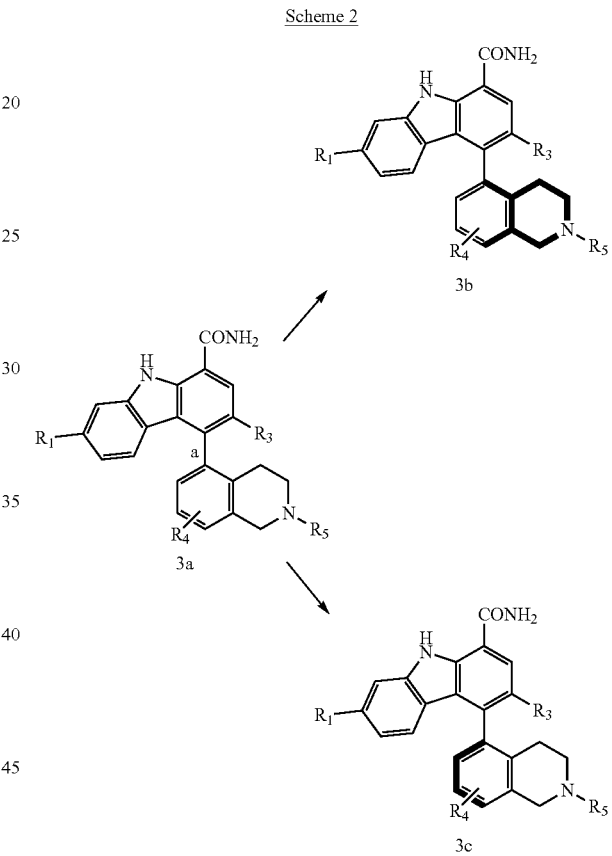

As shown in Scheme 2, steric hindrance can cause limited rotation about the bond labeled a, and compound 3a displays chirality, known as atropisomerism, and can exist as two enantiomers 3b and 3c. (In Scheme 2, Q is represented as a tetrahydroisoquinolin-5-yl group for illustrative purposes.) Under certain conditions, such as chromatography on a chiral stationary phase, the enantiomeric atropisomers can be observed as two separate peaks in the chromatogram. Such compounds can be isolated as mixtures of enantiomers, or the enantiomers can be separated using methods known in the art, such as preparative chromatography on a stationary phase. The separated enantiomers can be isolable and stable under appropriate storage and handling conditions.

In certain cases, a compound 3 is a tetrahydrocarbazolecarboxamide (where the dashed lines represent single bonds) and $R_{1a}$ and $R_{1b}$ are different from each other. One example is 3d, shown in Scheme 3, where $R_{1a}$ is other than hydrogen. (This example is illustrative only and is not meant to be limiting.) In this case, two chiral centers are present: the point of attachment of $R_{1a}$, and the bond labeled a as described above. Thus, four diastereomers are possible (3e, 3f, 3g and 3h). Compound 3d may therefore exist as a mixture of all four diastereomers, or as single diastereomers, or as mixtures of two or more diastereomers. Racemic mixtures of pairs of diastereomers (3e and 3h, or 3f and 3g) are possible. As described above, the diastereomers may be separated using methods known in the literature, such as chromatography on a chiral stationary phase.

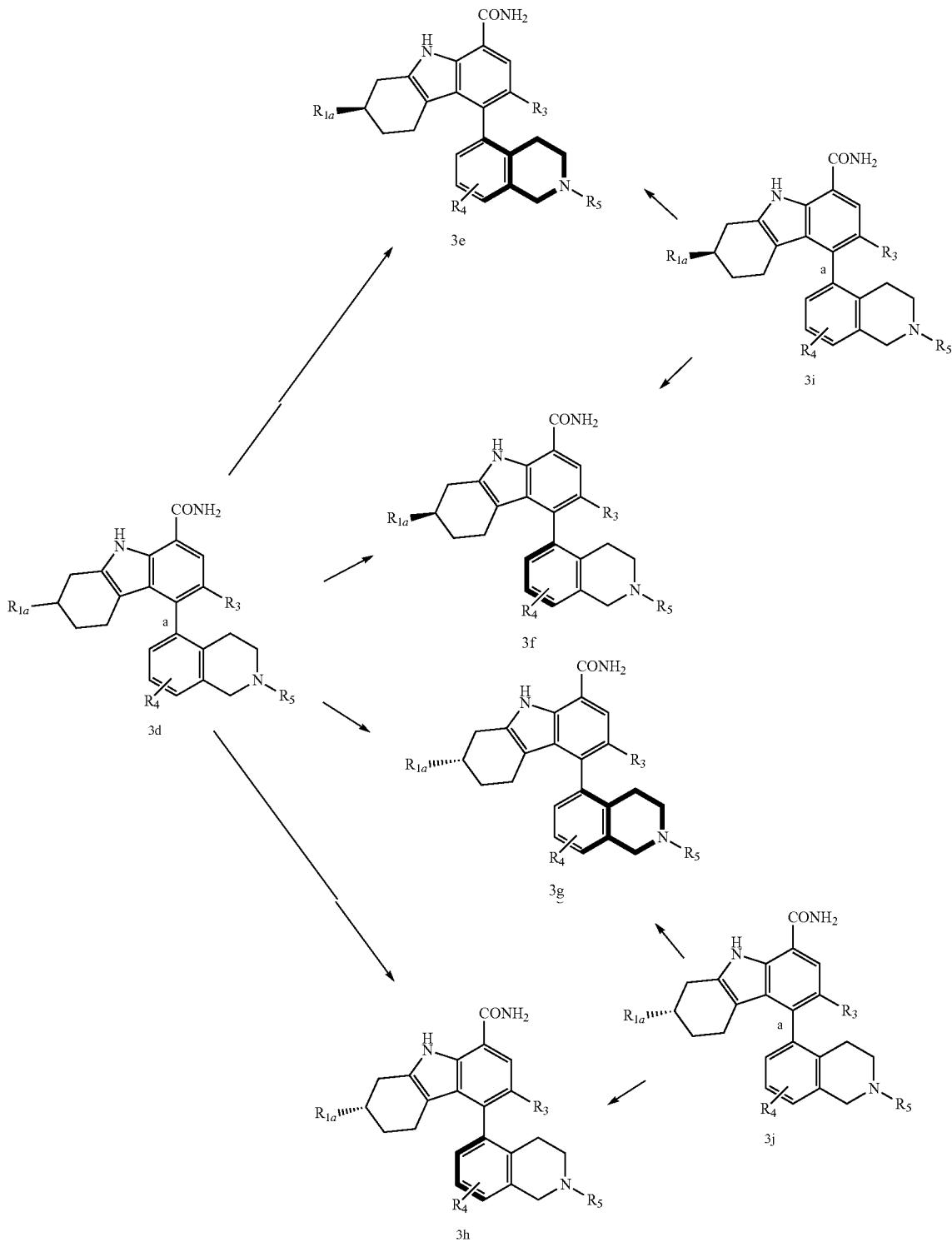

Scheme 3

In certain cases, a compound 3 can be prepared from a single enantiomer of a chiral tetrahydrocarbazolecarboxamide 1 or 4. In these cases, a mixture of two diastereomers can result from the Suzuki-Miyaura reaction which gives the compound 3. Example are 3i and 3j, shown in Scheme 3, where $R_1$, $R_3$ and $R_4$ are all other than hydrogen. (These examples are illustrative only and are not meant to be limiting.) Compound 3i, formed from one enantiomer of the appropriate compound 1 or 4, will be a mixture of diastereomers 3e and 3f, while compound 3j, formed from the other enantiomer of the appropriate compound 1 or 4, will be a mixture of diastereomers 3g and 3h. As described above, these diastereomers may be separated using methods known in the literature, such as chromatography or selective crystallization.

In some cases where 1 or 4 is a chiral tetrahydrocarbazolecarboxamide, chiral induction can occur during the Suzuki-Miyaura coupling reaction to provide a compound 3. In these cases, mixtures of diastereomers can be obtained which are not equimolar mixtures; that is, the compound 3 can be a mixture of diastereomers in which one or more of the diastereomers, having bond a with one absolute configuration, is present to a greater extent than one or more diastereomers having bond a with the opposite absolute configuration.

Certain compounds of Formula (I), represented by 7, can be prepared using methods illustrated in Scheme 4.

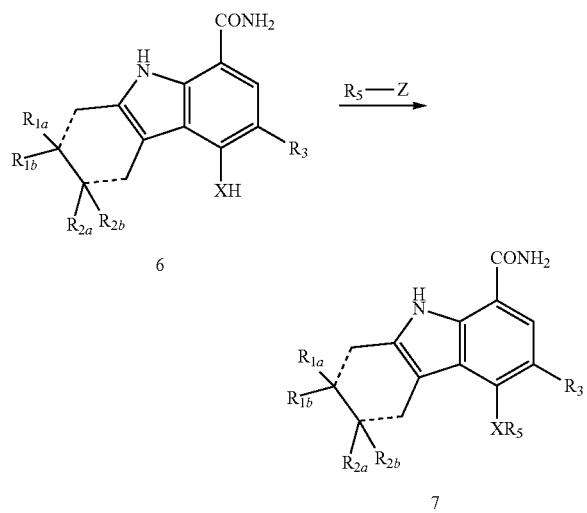

acid using any of a number of amide coupling reagents known in the literature, for example, (benzotriazol-1-yloxy)tris(dimethylamino) phosphonium hexafluorophosphate (also known as BOP or Castro's reagent), O-(7-azabenzotriazol-1-yl)-N,N,N',N'-tetramethyluronium hexafluorophosphate (also known as HATU), or a combination of N,N'-dicyclohexylcarbodiimide or 1-ethyl-3-(3-dimethylaminopropyl)carbodiimide hydrochloride (also known as EDC) and a reagent such as 1-hydroxybenzotriazole (also known as HOBT) or 1-hydroxy-7-azabenzotriazole (also known as HOAT). Such reactions are usually performed in a suitable solvent such as ethyl acetate, dichloromethane, tetrahydrofuran, N,N-dimethylformamide or N-methylpyrrolidin-2-one, in the presence of a suitable base such as triethylamine or diisopropylethylamine.

Certain compounds 6 of Scheme 4, where XH represents a group Q of Formula (I) wherein $R_5$ is replaced by H, can be prepared as shown in Scheme 5.

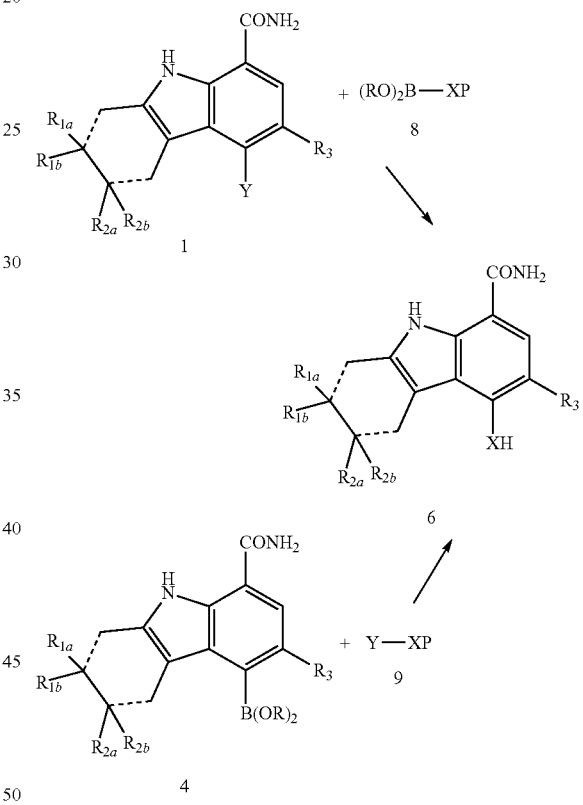

These methods involve reacting a compound 6 bearing a secondary amine (that is, where XH represents a group Q of Formula (I) wherein $R_5$ is replaced by H) with an appropriate reagent $R_5$—Z, where Z represents a leaving group such as Cl or OH, to provide a compound 7, where $XR_5$ represents one of the groups Q of Formula (I) resulting from such a reaction. Such reactions of amines are known in the literature. One example of such a reaction is acylation of the amine of a compound 6 with a carboxylic acid chloride or a carboxylic acid anhydride, usually performed in a suitable solvent such as tetrahydrofuran, ethyl acetate, acetonitrile, or dichloromethane, usually in the presence of a base such as triethylamine, diisopropylethylamine, pyridine, or an aqueous solution of an inorganic base such as sodium hydroxide or potassium carbonate. Alternatively, a solvent such as pyridine can be used, in which case the solvent can also serve as a base.

Another example of a reaction shown in Scheme 4 is acylation of the amine of a compound 6 with a carboxylic Reaction of a compound 1 with a boronic acid or boronic acid ester 8 (where XP is analogous to XH in Scheme 4; P can be either H or a suitable amine protecting group such as, for example, tert-butyloxycarbonyl (Boc) or benzyloxycarbonyl (Cbz), which are known in the literature as protecting groups for amines), using the Suzuki-Miyaura coupling as described above (Scheme 1), can provide a corresponding compound 6 after the removal of the protecting group P if necessary. If P in the compound 8 represents H, the compound 6 can be obtained directly.

By analogy to the methods illustrated in Scheme 1, an alternative method to prepare a compound 6 of Scheme 4, where XH represents a group Q of Formula (I) wherein $R_5$ is replaced by H, is also shown in Scheme 5. Reaction of a boronic acid or boronic acid ester 4 (where R is, for example, H, alkyl, or taken together form an optionally substituted 1,3,2-dioxaboralane or 1,3,2-dioxaborinane) of Scheme 1 with a compound 9, where Y is a suitable leaving group such as Br, Cl or trifluorosulfonyloxy, using the Suzuki-Miyaura coupling as described above, can also provide a compound 6. As described above, P can be H, or P can be a suitable protecting group in which case deprotection can provide the compound 6.

Also, a compound 8 can be prepared from a compound 9 using the same method described for the preparation of a compound 4 from a compound 1 (Scheme 1).

Compounds 1 (see Scheme 1) used in the preparation of compounds of Formula (I), can be prepared using procedures shown in Scheme 6.

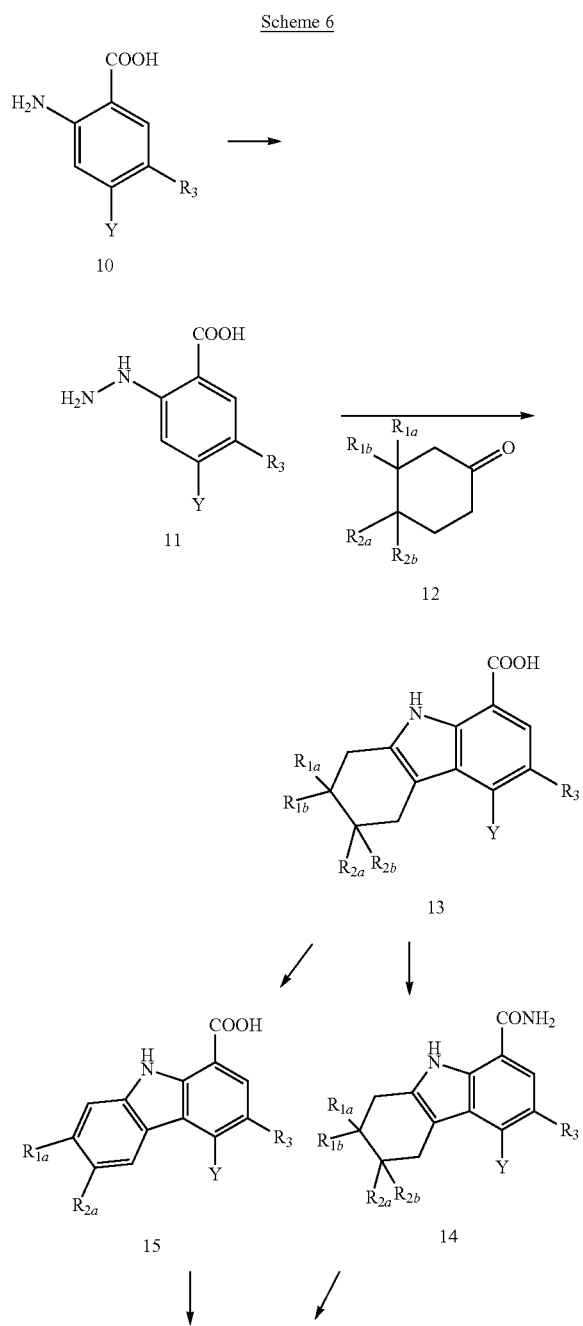

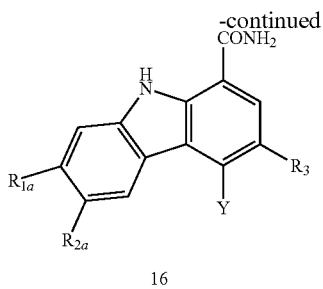

A substituted 2-aminobenzoic acid 10 (known in the literature, or prepared using procedures known in the literature) can be converted to the corresponding 2-hydrazinylbenzoic acid 11 as the hydrochloric acid salt using methods known in the literature, for example, by conversion to the corresponding diazonium salt by treatment with sodium nitrite in aqueous hydrochloric acid, followed by reduction with tin(II) chloride. Reaction of 11 with a suitable cyclohexanone 12 in a suitable solvent with an appropriate catalyst, for example, ethanol with hydrochloric acid, toluene with p-toluenesulfonic acid or trifluoroacetic acid, or acetic acid (in which case the solvent also can serve as the catalyst), can provide the corresponding substituted tetrahydrocarbazole 13. This reaction is commonly known as the Fischer indole synthesis, and is known in the chemical literature (for example, see Kamata, J. et al., *Chem. Pharm. Bull.*, 52:1071 (2004)). Alternatively, the Fischer indole synthesis can be carried out in two consecutive steps: 11 can react with 12 under suitable conditions (such as in an appropriate solvent such as ethanol or toluene, optionally with a suitable catalyst such as p-toluenesulfonic acid) to form an intermediate hydrazone, which can be isolated and then reacted further under suitable conditions (for example, ethanol with hydrochloric acid, acetic acid with zinc chloride, or toluene with trifluoroacetic acid) to provide a compound 13.

The carboxylic acid of a compound 13 can be converted to the corresponding carboxamide of compound 14 (which is an example of a compound 1 shown in Scheme 1) using methods known in the chemical literature, for example, by conversion of a compound 13 to the corresponding acid chloride by treatment with oxalyl chloride or thionyl chloride, followed by treatment with ammonia; or by treatment of a compound 13 with ammonia or ammonium chloride in the presence of a coupling reagent such as carbodiimide, or a mixture of EDC and HOAT. In cases of a compound 14 where $R_{1b}$ and $R_{2b}$ are both H, conversion of the compound 14 to the corresponding carbazole 16 (which is another example of a compound 1 shown in Scheme 1) can be performed using methods known in the chemical literature, for example, by treatment of the compound 14 with an oxidizing agent such as DDQ in a suitable solvent.

Alternatively, the order of the amide formation and oxidation steps can be reversed to convert a compound 13 (where both $R_{1b}$ and $R_{2b}$ are both H) to a compound 16. Thus, a compound 13 (where both $R_{1b}$ and $R_{2b}$ are both H) can be oxidized using the procedure described above, or a similar procedure, to give the corresponding compound 15. The carboxylic acid of the compound 15 can then be converted into the primary amide, again using a procedure described above or a similar procedure, to give the corresponding compound 16.

Compounds 13 and 14, where $R_{1a}$ and $R_{1b}$ are different from each other, contain a chiral center, and thus exist as two enantiomers. Preparation of compounds 13 and 14 as shown in Scheme 6 can provide racemic products, which may be used to prepare compounds of Formula (I) as shown in Scheme 1. Alternatively, compounds 13 and 14 may be resolved into separated enantiomers, using well-known methods such as chromatography on a chiral stationary phase.

literature, for example, Intermediates 47-2 and 48-1 and Example 73-1 in U.S. Pat. No. 8,084,620.) Some transformations of the carboxylic acid ester of a compound 17 into $R_{1a}$ and $R_{1b}$ are shown in Scheme 7; some of these as well as others are also illustrated in the examples of U.S. Pat. No. 8,084,620. Compounds 18, 20 and 22 in Scheme 7 are examples of Compound 1 shown in Scheme 1.

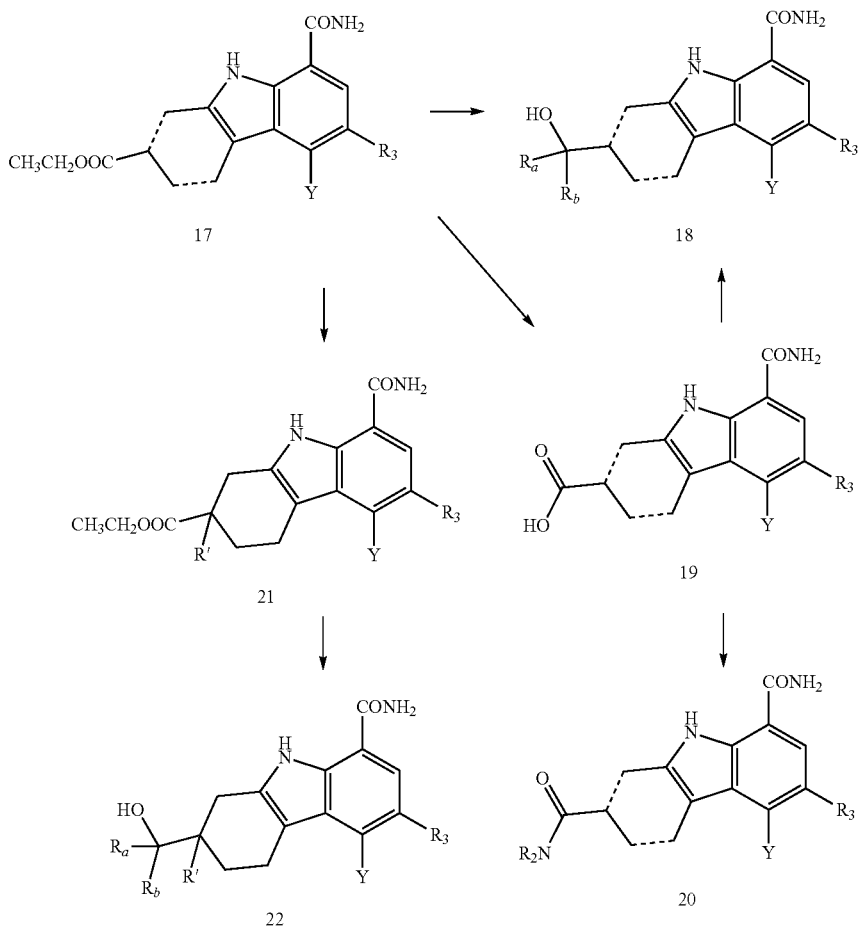

Scheme 7

It will be recognized by one skilled in the art of organic synthesis that some substituents $R_{1a}$ may be incompatible with reaction conditions used to prepare compounds of Formula (I) or intermediate compounds as shown in Schemes 1, 4, 5, and 6. In these cases, a different substituent may take the place of $R_{1a}$ during certain synthetic steps, and be converted into $R_{1a}$ at an appropriate stage of the synthesis using methods known in the chemical literature. Alternatively, in some cases a suitable protecting group may be used to protect $R_{1a}$ during certain synthetic steps, and removed at an appropriate stage of the synthesis. Such cases will be apparent to one skilled in the art. Some examples of such synthetic transformations are shown in Scheme 7.

A compound 1 shown in Scheme 1 bearing certain substituents $R_{1a}$ and $R_{1b}$ can be prepared from a precursor compound 17. A compound 17 can be prepared using the methods shown in Scheme 6 but substituting ethyl 3-oxo-cyclohexanecarboxylate for compound 12 in Scheme 6. (Some examples of compounds 17 are described in the The ester moiety of a compound 17 can be reduced to the corresponding primary carbinol of a compound 18 ($R_a$ and $R_b$ are both H) by treatment with a suitable reducing agent such as lithium aluminum hydride in a suitable solvent such as tetrahydrofuran. Alternatively, the ester moiety of a compound 17 can be converted to the corresponding tertiary carbinol of a compound 18 ($R_a$ and $R_b$ are both methyl) by treatment with a suitable reagent such as methylmagnesium chloride or methyllithium in a suitable solvent such as tetrahydrofuran.

The ester moiety of a compound 17 can be hydrolyzed to the corresponding carboxylic acid of a compound 19, for example, by treatment with aqueous lithium hydroxide or sodium hydroxide in a suitable co-solvent such as methanol, ethanol or tetrahydrofuran. The carboxylic acid moiety of a compound 19 can be converted to the secondary carbinol moiety of a compound 18 (one of $R_a$ and $R_b$ is H, and the other is methyl), for example, by conversion to the N,O-dimethylhydroxamate (commonly called a Weinreb amide)

followed by treatment with a reagent such as methylmagnesium chloride or methyllithium and subsequent reduction of the thus-formed ketone with a suitable reducing agent such as sodium borohydride. Alternatively, the carboxylic acid moiety of a compound 19 can be converted to the amide of a compound 20 using any of a variety of methods, such as conversion to the acid chloride followed by treatment with ammonia or a primary or secondary amine, or by treatment with ammonia or ammonium chloride or a primary or secondary amine in the presence of suitable coupling reagents such as HATU, BOP, or a combination of EDC with HOBT or HOAT.

In cases where the dotted lines of a compound 17 represent single bonds, the carbon atom bearing the ester moiety can be alkylated by treatment of the compound 17 with a base such as lithium bis(trimethylsilyl)amide or lithium diisopropylamide in a suitable solvent such as tetrahydrofuran, and treatment of the resulting anion with an alkylating agent such as iodomethane to give a compound 21 where R' is methyl. The ester moiety of the compound 21 can then be converted to the carbinol moiety of a compound 22 (where $R_a$ and $R_b$ are both H, both methyl or one is H and the other is methyl) by the same methods used to prepare a compound 18 as described above.

Certain compounds 1 of Scheme 1, used to prepare compounds of Formula (I), may also be prepared using procedures shown in Scheme 8.

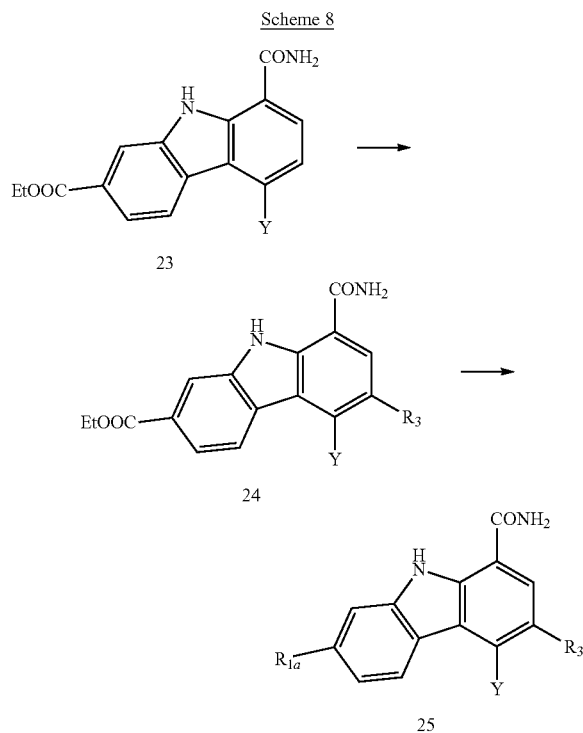

A compound 23, prepared from the appropriate 2-hydrazinylbenzoic acid as shown in Scheme 6 (see, for example, U.S. Pat. No. 8,084,620, Intermediate 48-1) can be treated with an appropriate halogenating reagent to give a compound 24, where $R_3$ is a halogen atom. For example, treatment of a compound 23 with a chlorinating reagent such as N-chlorosuccinimide can give the compound 24 where $R_3$ is Cl, and treatment of a compound 23 with a fluorinating reagent such as 1-(chloromethyl)-4-fluoro-1,4-diazoniabicyclo[2.2.2]octane-bis (tetrafluoroborate) [SELECTFLUOR®] can give the compound 24 where $R_3$ is F. Conversion of a compound 24 to a corresponding compound 25 (which is an example of a compound 1 of Scheme 1) can be achieved using methods known in the literature, some of which are described in the discussion of Scheme 7.

As shown in Scheme 9, a compound 26 can be converted to a compound 27, which is an example of a compound 5 of Scheme 1. Analogously, a compound 28 can be converted to a compound 29, which is an example of a compound 2 of Scheme 1.

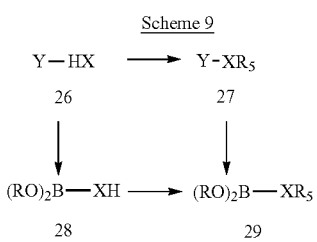

In Scheme 11, Y represents a suitable group such as Br, Cl or trifluoromethanesulfonyloxy; $(RO)_2B$ represents a boronic acid or boronic acid ester; and XH represents a group Q of Formula (I) where $R_5$ is replaced by H. Conversion of a compound 26 to a compound 27, and conversion of a compound 28 to a compound 29, can be accomplished using the same methods described for the analogous transformations of a compound 6 to a compound 7 in Scheme 4. Also, conversion of a compound 26 to a compound 28, and conversion of a compound 27 to a compound 29, can be accomplished using the methods described for the transformation of a compound 1 to a compound 4 in Scheme 1.

In some cases, when the conversion of an intermediate compound into another intermediate compound or a compound of Formula (I) requires more than one synthetic reaction, the order of the individual steps can be changed. Such cases will be recognized by one skilled in the art of organic synthesis. One example is shown in Scheme 9. Conversion of a compound 26 to a compound 29 can be done by (1) conversion of the amine of a compound 26 to the substituted amine of a compound 27, followed by (2) conversion of the group Y of the compound 27 to the boronic acid or boronic acid ester of the compound 29. Alternatively, the same conversion of a compound 26 to a compound 29 can be done by (1) conversion of the group Y of a compound 26 to the boronic acid or boronic acid ester of a compound 28, followed by (2) conversion of the amine of the compound 28 to the substituted amine of the compound 29. Another example is shown in Scheme 6. Conversion of a compound 13 to a compound 16 can be done by (1) conversion of the carboxylic acid of a compound 13 to the carboxamide of a compound 14, followed by (2) oxidation of the compound 14 to the carbazole 16. Alternatively, the same conversion of a compound 13 to a compound 16 can be done by (1) oxidation of a compound 13 to the carbazole 15, followed by (2) conversion of the carboxylic acid of the compound 15 to the carboxamide of the compound 16.

EXAMPLES

Compounds of the current invention, and intermediates used in the preparation of compounds of the current invention, can be prepared using procedures shown in the following Examples and related procedures. The methods and conditions used in these Examples, and the actual compounds prepared in these Examples, are not meant to be limiting, but are meant to demonstrate how the compounds of the current invention can be prepared. Starting materials and reagents used in these Examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the Examples given, the phrase "dried and concentrated" generally refers to removal of most residual water from a solution in an organic solvent using either anhydrous sodium sulfate or magnesium sulfate, followed by filtration and removal of the solvent from the filtrate (generally under reduced pressure and at a temperature suitable to the stability of the material being prepared). Column chromatography was generally performed using the flash chromatography technique (Still, W. et al., *J. Org. Chem.*, 43:2923 (1978)), or with pre-packed silica gel cartridges using an Isco medium pressure chromatography apparatus (Teledyne Corporation), eluting with the solvent or solvent mixture indicated. Preparative high pressure liquid chromatography (HPLC) was performed using a reverse phase column (Waters SunFire $C_{18}$, Waters XBridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Supercritical fluid chromatography (SFC), a form of normal phase HPLC using a mobile phase containing super- or subcritical fluid $CO_2$ and polar organic modifiers such as alcohols, was used to separate chiral compounds. (White, C. et al., *J. Chromatography A*, 1074:175 (2005)). Chiral SFC separation of enantiomers or diastereomers was performed using conditions described for the individual cases. Mass spectral data were obtained by liquid chromatography-mass spectrometry using electrospray ionization.

Single crystal x-ray diffraction data were collected on a Bruker-AXS APEX2 CCD system using Cu Kα radiation (λ=1.5418 Å). Indexing and processing of the measured intensity data were carried out with the APEX2 software package/program suite (see the APEX2 User Manual, v 1.27; Bruker AXS, Inc., WI 53711 USA). When indicated, crystals were cooled in the cold stream of an Oxford Cryosystems cryostream cooler (Cosier, J. et al., *J. Appl. Cryst.*, 19:105 (1986)) during data collection. The structures were solved by direct methods and refined on the basis of observed reflections using the crystallographic package SHELXTL (see the APEX2 User Manual, v 1.27; Bruker AXS, Inc., WI 53711 USA). The derived atomic parameters (coordinates and temperature factors) were refined through full matrix least-squares. The function minimized in the refinements was $\Sigma_W(|F_O|-|F_C|)^2$. R is defined as $\Sigma||F_O|-|F_C||/\Sigma|F_O|$ while $R_W=[\Sigma_W(|F_O|-|F_C|)^2/\Sigma_W|F_O|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied. Unit cell parameters were obtained according to the procedure described in Stout et al., *X-Ray Structure Determination: A Practical Guide*, MacMillan (1968).

Chemical names were determined using ChemBioDraw Ultra, version 12.0 (CambridgeSoft).

Abbreviations

Ac acetyl
ACN acetonitrile
AcOH acetic acid
aq. aqueous
anhyd. anhydrous
Boc tert-butyloxycarbonyl
BOP benzotriazol-1-yloxy)tris(dimethylamino)phosphonium hexafluorophosphate
Cbz benzyloxycarbonyl
Conc. concentration
DCM dichloromethane
DDQ 2,3-dichloro-5,6-dicyano-1,4-benzoquinone
DIEA diisopropylethylamine
DMF N,N-dimethylformamide
DMSO dimethyl sulfoxide
dppf 1,1'-bis(diphenylphosphino)ferrocene
EDC 1-[3-(dimethylamino)propyl]-3-ethyl-carbodiimide hydrochloride
eq. or Eq. or equiv. equivalent(s)
EtOAc ethyl acetate
h or hr hour(s)
HATU O-(7-azabenzotriazol-1-yl)-1,1,3,3-tetramethyluronium hexafluorophosphate
HOAT 1-hydroxy-7-azabenzotriazole
HOBT 1-hydroxybenzotriazole
LC liquid chromatography
LCMS or LC/MS liquid chromatograph mass spectrometry
Me methyl
MeOH methanol
MHz megahertz
min. minute(s)
$M^+$ $(M+H)^+$
$M^{+1}$ $(M+H)^+$
MS mass spectrometry
m/z mass to charge ratio
N Normal
NMP N-methylpyrrolidinone
NMR nuclear magnetic resonance
ppm parts per million
Ret Time or Rt retention time
sat. or sat'd. saturated
sec second(s)
TFA trifluoroacetic acid
THF tetrahydrofuran

Intermediate 1

(RS)-5-Bromo-6-fluoro-2-(trifluoromethyl)-2,3,4,9-tetrahydro-1H-carbazole-8-carboxamide

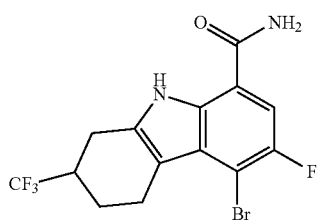

(I-1)

Intermediate 1A: 4-Bromo-2,5-difluorobenzoic Acid

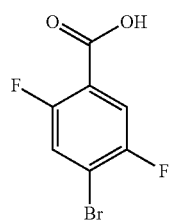

(I-1A)

A solution of 1,4-dibromo-2,5-difluorobenzene (640 mg, 2.35 mmol) in dry diethyl ether (10 mL) cooled in a dry ice-acetone bath was treated dropwise with 2.5 M n-butyllithium in hexanes (1.04 mL, 2.59 mmol). The solution was stirred at −78° C. for 30 min, then was treated with a piece of dry ice. The cooling bath was removed after 5 min and the mixture was stirred for another 30 min while warming to room temperature. The mixture was diluted with EtOAc and water. The organic phase was separated and washed twice with saturated aqueous NaHCO₃. The combined aqueous phases were acidified with 1 M aqueous HCl, extracted twice with DCM, and the combined organic phases were dried and concentrated to give 4-bromo-2,5-difluorobenzoic acid as a white solid (297 mg, 53% yield).

Intermediate 1B: 4-Bromo-5-fluoro-2-hydrazinylbenzoic Acid Hydrochloride

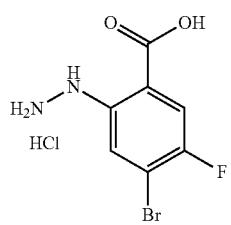

(I-1B)

A mixture of 4-bromo-2,5-difluorobenzoic acid (2.50 g, 10.6 mmol) and hydrazine (3.81 mL, 121 mmol) in N-methyl-2-pyrrolidinone (2 mL) was heated at 95° C. for 4 h. The cooled mixture was poured into vigorously stirred 6 M aqueous HCl (400 mL) which was cooled in a NaCl-ice bath. The resulting precipitate was collected by filtration, washed with 6 M aqueous HCl (200 mL) and dried under vacuum to give 4-bromo-5-fluoro-2-hydrazinylbenzoic acid hydrochloride as a yellow solid (1.88 g, 71% purity, 44% yield), used without further purification.

Alternative Synthesis of Intermediate 1B:

A suspension of 2-amino-4-bromo-5-fluorobenzoic acid (10.0 g, 42.7 mmol) in a mixture of 37% aqueous HCl (42.7 mL) and water (14.3 mL), stirred on a NaCl-ice bath, was treated dropwise with a solution of sodium nitrite (3.24 g, 47.0 mmol) in water (15.7 mL). When addition was complete, the mixture was stirred for 30 min more. A solution of tin(II) chloride dihydrate (28.9 g, 128 mmol) in 37% aqueous HCl (27.5 mL) was added dropwise. The cooling bath was removed and the mixture was stirred at room temperature for 45 min. The thick suspension was filtered and the collected precipitate was washed thoroughly with water and dried overnight under reduced pressure. The solid was triturated with MeOH with sonication, and the precipitate was collected by filtration, washed with MeOH and dried. The filtrate was concentrated, and the residue was triturated with DCM. The resulting solid was collected by filtration and dried, and the two solids were combined to give 4-bromo-5-fluoro-2-hydrazinylbenzoic acid hydrochloride (5.37 g, 44% yield) as a white solid. Mass spectrum m/z 249, 251 (M+H)⁺.

Intermediate 1C: 5-Bromo-6-fluoro-2-(trifluoromethyl)-2,3,4,9-tetrahydro-1H-carbazole-8-carboxylic Acid

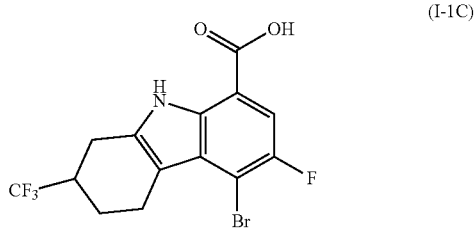 [SMILES: O=C(O)c1cc(F)c(Br)c2c3c([nH]c12)CC(C(F)(F)F)CC3]

(I-1C)

A mixture of 4-bromo-5-fluoro-2-hydrazinylbenzoic acid hydrochloride (5.00 g, 17.5 mmol), and (RS)-3-trifluoromethylcyclohexanone (4.07 g, 24.5 mmol) in acetic acid (8.0 mL) was stirred at 78° C. for 18 h. The mixture was cooled to room temperature and concentrated. The residue was suspended in EtOAc and the precipitate was collected by filtration and dried. The filtrate was concentrated and the residue was suspended in DCM. The precipitate was collected by filtration and dried, and the two precipitates were combined to provide 5-bromo-6-fluoro-2-(trifluoromethyl)-2,3,4,9-tetrahydro-1H-carbazole-8-carboxylic acid as light orange solid (4.10 g, 55% yield). Mass spectrum m/z 380, 382 (M+H)⁺.

Intermediate 1

A solution of 5-bromo-6-fluoro-2-(trifluoromethyl)-2,3,4,9-tetrahydro-1H-carbazole-8-carboxylic acid (2.00 g, 5.26 mmol), NH₄Cl (2.81 g, 52.6 mmol) and HATU (2.20 g, 5.79 mmol) in DMF (25 mL) was treated with triethylamine (3.67 mL, 26.3 mmol) and the mixture was stirred at room temperature for 90 min. Ice water (30 mL) was added and the mixture was stirred for 30 min. The precipitate was collected by filtration and washed with water (60 mL). The collected solid was twice suspended in toluene (30 mL) and concentrated under vacuum, then dried. The residue was subjected to column chromatography on silica gel, eluting with 10% MeOH/EtOAc-hexanes (gradient from 0-100%), to provide 5-bromo-6-fluoro-2-(trifluoromethyl)-2,3,4,9-tetrahydro-1H-carbazole-8-carboxamide as a light yellow solid (1.55 g, 74% yield). Mass spectrum m/z 379, 381 (M+H)⁺. ¹H NMR (400 MHz, MeOH-d₄) δ 7.46 (d, J=9.9 Hz, 1H), 3.46 (dd, J=16.1, 4.4 Hz, 1H), 3.11 (dd, J=16.4, 5.3 Hz, 1H), 3.06-2.93 (m, 1H), 2.92-2.80 (m, 1H), 2.79-2.59 (m, 1H), 2.37-2.23 (m, 1H), 1.86-1.65 (m, 1H).

Intermediate 2

5-Bromo-3,3,6-trifluoro-2,3,4,9-tetrahydro-1H-carbazole-8-carboxamide

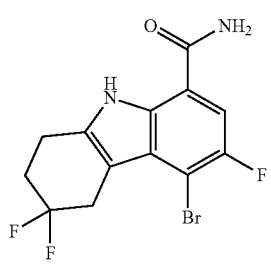

(I-2)

Following the procedures used to convert Intermediate 1B into Intermediate 1, 4,4-difluorocyclohexanone was converted into 5-bromo-3,3,6-trifluoro-2,3,4,9-tetrahydro-1H-carbazole-8-carboxamide. Mass spectrum m/z 347, 349 (M+H)⁺. ¹H NMR (400 MHz, DMSO-d₆) δ 11.34 (s, 1H), 8.12 (br. s., 1H), 7.64 (d, J=10.1 Hz, 1H), 7.57 (br. s., 1H), 3.54 (t, J=14.4 Hz, 2H), 2.97 (t, J=6.6 Hz, 2H), 2.31 (tt, J=13.9, 6.7 Hz, 2H).

Intermediate 3

4-Bromo-3-fluoro-9H-carbazole-1-carboxamide

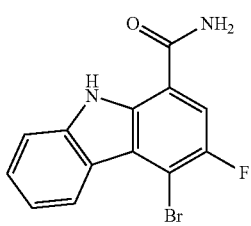

(I-3)

Intermediate 3A: 5-Bromo-6-fluoro-2,349-tetrahydro-1H-carbazole-8-carboxylic Acid

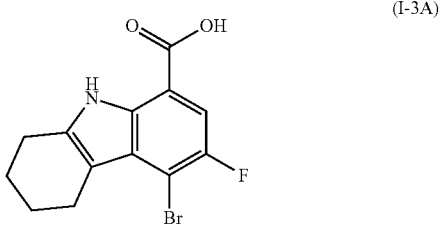 [SMILES: O=C(O)c1cc(F)c(Br)c2c3c([nH]c12)CCCC3]

(I-3A)

A mixture of 4-bromo-5-fluoro-2-hydrazinylbenzoic acid hydrochloride [Intermediate 1B] (12.0 g, 42.0 mmol) and cyclohexanone (12.4 g, 126 mmol) in acetic acid (90 mL) was stirred at 90° C. overnight. The mixture was cooled to room temperature and the precipitate was collected by filtration, washed with water and dried to provide 5-bromo-6-fluoro-2,3,4,9-tetrahydro-1H-carbazole-8-carboxylic acid (5.02 g, 16.1 mmol, 38% yield) as a light yellow solid. Mass spectrum m/z 312, 314 (M+H)⁺.

Intermediate 3B:
4-Bromo-3-fluoro-9H-carbazole-1-carboxylic Acid

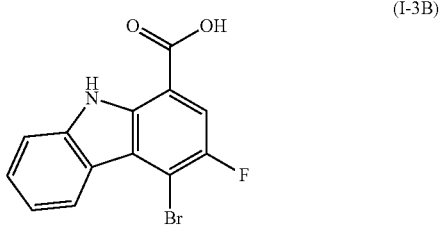 [SMILES: O=C(O)c1cc(F)c(Br)c2c1[nH]c1ccccc12]

(I-3B)

A mixture of 5-bromo-6-fluoro-2,3,4,9-tetrahydro-1H-carbazole-8-carboxylic acid (5.00 g, 16.0 mmol) and DDQ (8.00 g, 35.2 mmol) in THF (60 mL) was stirred at 60° C. for 3 h. The mixture was cooled to room temperature, diluted with EtOAc, washed sequentially with saturated aqueous NaHCO₃, water, and 1 M aqueous HCl, dried and concentrated to provide crude 4-bromo-3-fluoro-9H-carbazole-1-carboxylic acid (5.30 g, 86% yield, 80% purity), which was used without further purification.

Intermediate 3

A mixture of 4-bromo-3-fluoro-9H-carbazole-1-carboxylic acid (4.70 g, 15.3 mmol), HOBT (2.34 g, 15.3 mmol) and EDC (2.92 g, 15.3 mmol) in THF (70 mL) was stirred at room temperature for 30 min. Aqueous ammonium hydroxide (0.891 mL, 22.9 mmol) was added and the mixture was stirred at room temperature overnight. The mixture was concentrated and the residue was dissolved in EtOAc, washed twice with water, then with saturated aqueous NaHCO₃, dried and concentrated. The residue was triturated with DCM to provide 4-bromo-3-fluoro-9H-carbazole-1-carboxamide as a light brown solid (3.40 g, 73% yield). Mass spectrum m/z 307, 309 (M+H)⁺, 290, 292 (M+H—NH₃)⁺. ¹H NMR (400 MHz, MeOH-d₄) δ 8.73 (dd, J=8.1, 0.9 Hz, 1H), 7.83 (d, J=9.9 Hz, 1H), 7.69-7.63 (m, 1H), 7.54 (ddd, J=8.2, 7.1, 1.2 Hz, 1H), 7.29 (ddd, J=8.1, 7.1, 1.0 Hz, 1H).

Intermediate 4

4-Bromo-3-fluoro-7-(trifluoromethyl)-9H-carbazole-1-carboxamide

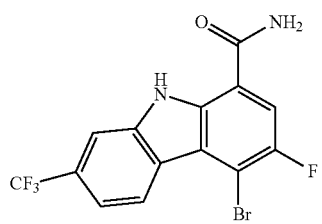

Following the procedures used to convert Intermediate 3A into Intermediate 3, 5-bromo-6-fluoro-2-(trifluoromethyl)-2,3,4,9-tetrahydro-1H-carbazole-8-carboxylic acid [Intermediate 1C] was converted into 4-bromo-3-fluoro-7-(trifluoromethyl)-9H-carbazole-1-carboxamide. Mass spectrum m/z 416, 418 (M+H+CH$_3$CN)$^{30}$. $^1$H NMR (400 MHz, MeOH-d$_4$) δ 8.83 (d, J=8.6 Hz, 1H), 8.00 (d, J=0.7 Hz, 1H), 7.89 (d, J=9.8 Hz, 1H), 7.52 (dd, J=8.4, 1.1 Hz, 1H).

Intermediate 5

(RS)-5-Bromo-6-fluoro-2-(2-hydroxypropan-2-yl)-2,3,4,9-tetrahydro-1H-carbazole-8-carboxamide

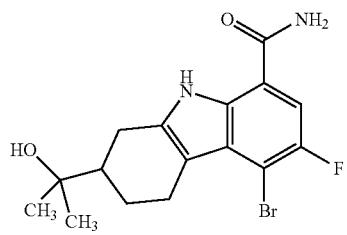

Intermediate 5A: (RS)-5-Bromo-2-(ethoxycarbonyl)-6-fluoro-2,3,4,9-tetrahydro-1H-carbazole-8-carboxylic Acid

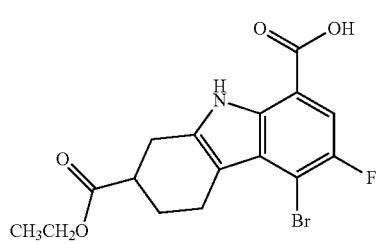

A mixture of 4-bromo-5-fluoro-2-hydrazinylbenzoic acid hydrochloride [Intermediate 1B] (5.37 g, 18.8 mmol), ethyl (RS)-3-oxocyclohexanecarboxylate (3.52 g, 20.7 mmol) and acetic acid (3.23 mL, 56.4 mmol) in toluene (90 mL) was heated at 110° C. for 20 h. The solvent was removed under reduced pressure, and the residue was diluted with toluene (43 mL) and TFA (11 mL). The mixture was stirred at 90-94° C. overnight. The cooled mixture was diluted with EtOAc, sonicated, and the precipitate was collected by filtration. The filtrate was concentrated and the residue was suspended in EtOAc with sonication, resulting in another precipitate which was also collected by filtration and washed with EtOAc. The combined solids were triturated twice with MeOH to give a solid. The combined filtrates were concentrated and the residue was triturated with MeOH to give additional solid. The solids were combined to give (RS)-5-bromo-2-ethoxycarbonyl-6-fluoro-2,3,4,9-tetrahydro-1H-carbazole-8-carboxylic acid as a pale yellow solid (3.38 g). Mass spectrum m/z 384, 386 (M+H)$^+$.

Intermediate 5B: Ethyl (RS)-5-bromo-8-carbamoyl-6-fluoro-2,3,4,9-tetrahydro-1H-carbazole-2-carboxylate

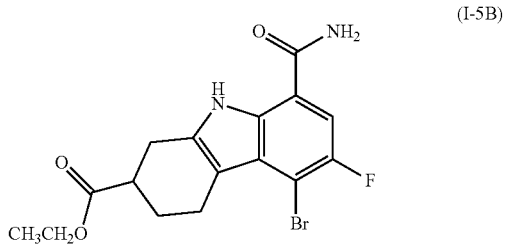

A mixture of (RS)-5-bromo-2-(ethoxycarbonyl)-6-fluoro-2,3,4,9-tetrahydro-1H-carbazole-8-carboxylic acid (0.513 g, 1.34 mmol), EDC (0.384 g, 2.00 mmol), and HOBT (0.307 g, 2.00 mmol) in THF (10 mL) and DCM (1.7 mL) was stirred at room temperature for 20 min. Aqueous NH$_4$OH (28%, 0.078 mL, 2.00 mmol) was added, and the mixture was stirred at room temperature for 60 min. The mixture was diluted with EtOAc and washed twice with saturated aqueous NaHCO$_3$, then with brine. The aqueous layers were extracted with EtOAc, and the combined organic layers were dried and concentrated. The residue was triturated in MeOH with sonication to provide ethyl (RS)-5-bromo-8-carbamoyl-6-fluoro-2,3,4,9-tetrahydro-1H-carbazole-2-carboxylate as a yellow solid (0.432 g, 84% yield). Mass spectrum m/z 383, 385 (M+H)$^+$.

Intermediate 5

A solution of ethyl (RS)-5-bromo-8-carbamoyl-6-fluoro-2,3,4,9-tetrahydro-1H-carbazole-2-carboxylate (10.0 g, 26.1 mmol) in THF (200 mL) at −78° C. was treated dropwise over 30 min with 1.6 M methyllithium in ether (49 mL, 78 mmol). The mixture was stirred at −78° C. for 45 min, then was treated with additional methyllithium solution (33 mL) over 25 min. The mixture was stirred at −78° C. for an additional 90 min, then was treated with saturated aqueous NH$_4$Cl and warmed to room temperature. The mixture was diluted with EtOAc and washed sequentially with water and brine. The aqueous layers were extracted with EtOAc. The combined organic layers were dried and concentrated. The residue was dissolved in EtOAc (about 100 mL) and filtered through a pad of CELITE® topped with a pad of silica gel. The CELITE® and silica gel were washed further with EtOAc (about 1000 mL). Concentration of the combined filtrates gave (RS)-5-bromo-6-fluoro-2-(2-hydroxypropan-2-yl)-2,3,4,9-tetrahydro-1H-carbazole-8-carboxamide as a pale yellow solid (9.24 g, 96% yield). Mass spectrum m/z 369, 371 (M+H)+.

Intermediates 6 and 7

(R)-5-Bromo-6-fluoro-2-(2-hydroxypropan-2-yl)-2,3,4,9-tetrahydro-1H-carbazole-8-carboxamide (I-6), and (S)-5-Bromo-6-fluoro-2-(2-hydroxypropan-2-yl)-2,3,4,9-tetrahydro-1H-carbazole-8-carboxamide (I-7)

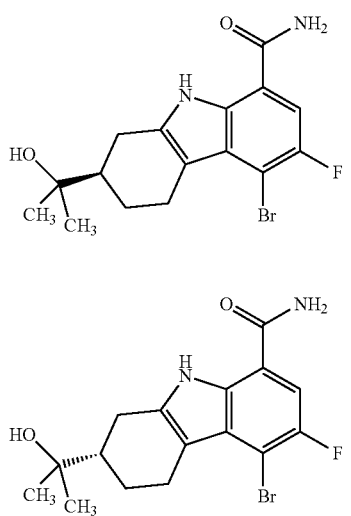

A sample of (RS)-5-bromo-6-fluoro-2-(2-hydroxypropan-2-yl)-2,3,4,9-tetrahydro-1H-carbazole-8-carboxamide [Intermediate 5] was separated by chiral super-critical fluid chromatography (Column: CHIRALPAK® OD-H (3×25 cm, 5 m); Mobile Phase: $CO_2$-MeOH (70:30) at 150 mL/min, 40° C.). The first peak eluting from the column provided (R)-5-bromo-6-fluoro-2-(2-hydroxypropan-2-yl)-2,3,4,9-tetrahydro-1H-carbazole-8-carboxamide [Intermediate 6]. The second peak eluting from the column provided (S)-5-bromo-6-fluoro-2-(2-hydroxypropan-2-yl)-2,3,4,9-tetrahydro-1H-carbazole-8-carboxamide [Intermediate 7]. The mass spectra and $^1$H NMR spectra of the two enantiomers were the same. Mass spectrum m/z 369, 371 (M+H)+. $^1$H NMR (500 MHz, DMSO-$d_6$) δ 10.96 (s, 1H), 8.07 (br. s., 1H), 7.55 (d, J=10.3 Hz, 1H), 7.50 (br. s., 1H), 4.24 (s, 1H), 3.26 (dd, J=15.8, 4.4 Hz, 1H), 2.93 (dd, J=17.1, 4.6 Hz, 1H), 2.72 (t, J=11.7 Hz, 1H), 2.48-2.40 (m, 1H), 2.12 (d, J=9.2 Hz, 1H), 1.70-1.62 (m, 1H), and 1.32 (qd, J=12.4, 5.3 Hz, 1H).

Alternative Super-Critical Fluid Chromatography Separation:

A sample of (RS)-5-bromo-6-fluoro-2-(2-hydroxypropan-2-yl)-2,3,4,9-tetrahydro-1H-carbazole-8-carboxamide [Intermediate 5] was separated by chiral super-critical fluid chromatography (Column: CHIRALPAK® AD-H (3×25 cm, 5 μm); Mobile Phase: $CO_2$-MeOH (55:45) at 150 mL/min, 40° C.). The first peak eluting from the column provided (S)-5-bromo-6-fluoro-2-(2-hydroxypropan-2-yl)-2,3,4,9-tetrahydro-1H-carbazole-8-carboxamide [Intermediate 7]. The second peak eluting from the column provided (R)-5-bromo-6-fluoro-2-(2-hydroxypropan-2-yl)-2,3,4,9-tetrahydro-1H-carbazole-8-carboxamide [Intermediate 6].

Intermediate 8

6-Fluoro-2-(S)-(2-hydroxypropan-2-yl)-5-(RS)-(1,2,3,4-tetrahydroisoquinolin-5-yl)-2,3,4,9-tetrahydro-1H-carbazole-8-carboxamide (Mixture of Diastereomers)

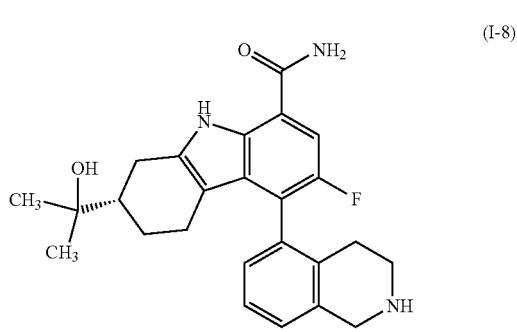 [SMILES: CC(C)(O)[C@H]1CCc2c([nH]c3c(C(N)=O)cc(F)c(-c4cccc5c4CCNC5)c23)C1]

Intermediate 8A: tert-Butyl 5-(4,4,5,5-tetramethyl-1,3,2-dioxaborolan-2-yl)-3,4-dihydroisoquinoline-2(1H)-carboxylate

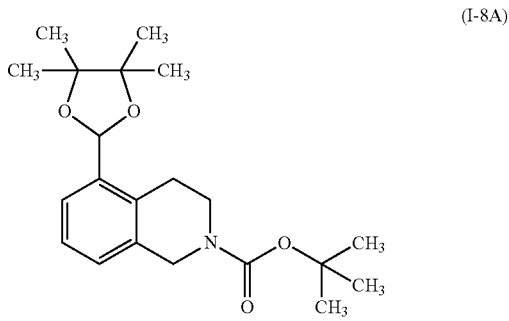 [SMILES: CC(C)(C)OC(=O)N1CCc2c(cccc2C2OC(C)(C)C(C)(C)O2)C1]

A mixture of tert-butyl 5-bromo-3,4-dihydroisoquinoline-2(1H)-carboxylate (0.500 g, 1.60 mmol) and 4,4,4',4',5,5,5',5'-octamethyl-2,2'-bi(1,3,2-dioxaborolane) (0.488 g, 1.92 mmol) in DMF (8 mL) was subjected to 3 evacuate-fill cycles with nitrogen. Potassium acetate (0.472 g, 4.80 mmol) and $PdCl_2$(dppf) DCM complex (0.117 g, 0.160 mmol) were added, the mixture was subjected to 2 more evacuate-fill cycles with nitrogen, and heated 90° C. overnight under a nitrogen atmosphere. The mixture was cooled to room temperature, diluted with EtOAc, washed sequentially with water, 10% aqueous LiCl and saturated brine, dried and concentrated. The residue was subjected to column chromatography on silica gel, eluting with EtOAc-hexanes, to provide tert-butyl 5-(4,4,5,5-tetramethyl-1,3,2-dioxaborolan-2-yl)-3,4-dihydroisoquinoline-2(1H)-carboxylate as a white solid (0.514 g, 89% yield). Mass spectrum m/z 360 (M+H)+.

Intermediate 8B: tert-Butyl 5-(RS)-(8-carbamoyl-6-fluoro-2-(S)-(2-hydroxypropan-2-yl)-2,3,4,9-tetrahydro-1H-carbazol-5-yl)-3,4-dihydroisoquinoline-2(1H)-carboxylate (Mixture of Diastereomers)

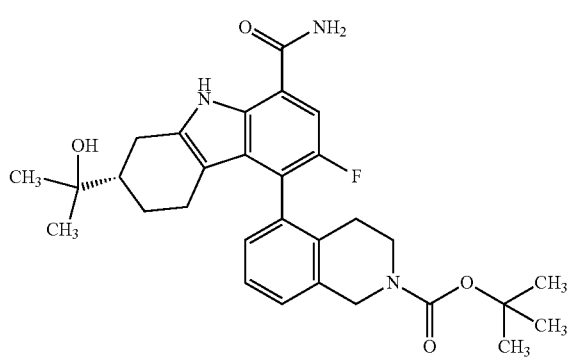

(I-8B)

A mixture of (S)-5-bromo-6-fluoro-2-(2-hydroxypropan-2-yl)-2,3,4,9-tetrahydro-1H-carbazole-8-carboxamide [Intermediate 7] (0.155 g, 0.420 mmol), tert-butyl 5-(4,4,5,5-tetramethyl-1,3,2-dioxaborolan-2-yl)-3,4-dihydroisoquinoline-2(1H)-carboxylate (0.181 g, 0.504 mmol), 2 M aqueous $K_3PO_4$ (0.630 mL, 1.26 mmol) and THF (3 mL) was subjected to 3 evacuate-fill cycles with nitrogen. The mixture was treated with 1,1'-bis(di-tert-butylphosphino)ferrocene palladium dichloride (0.014 g, 0.021 mmol) and the mixture was subjected to 2 more evacuate-fill cycles with nitrogen. The mixture was stirred at room temperature overnight, then was diluted with EtOAc, washed sequentially with water and saturated brine, dried and concentrated. The residue was subjected to column chromatography on silica gel, eluting with EtOAc-hexanes (gradient from 50-70%), to provide tert-butyl 5-(RS)-(8-carbamoyl-6-fluoro-2-(S)-(2-hydroxypropan-2-yl)-2,3,4,9-tetrahydro-1H-carbazol-5-yl)-3,4-dihydroisoquinoline-2(1H)-carboxylate, a mixture of diastereomers, as an off-white solid (0.178 g, 81% yield). Mass spectrum m/z 522 (M+H)+.

Intermediate 8

A mixture of tert-butyl 5-(RS)-(8-carbamoyl-6-fluoro-2-(S)-(2-hydroxypropan-2-yl)-2,3,4,9-tetrahydro-1H-carbazol-5-yl)-3,4-dihydroisoquinoline-2(1H)-carboxylate (mixture of diastereomers) (0.178 g, 0.341 mmol) and TFA (5 mL) was stirred at room temperature for 30 min. The mixture was concentrated and the residue was diluted with EtOAc, washed sequentially with 1.5 M aqueous $K_2HPO_4$ and saturated brine, and dried and concentrated to provide 6-fluoro-2-(S)-(2-hydroxypropan-2-yl)-5-(RS)-(1,2,3,4-tetrahydroisoquinolin-5-yl)-2,3,4,9-tetrahydro-1H-carbazole-8-carboxamide, a mixture of diastereomers, which was used without further purification. Mass spectrum m/z 422 (M+H)+.

Intermediates 9 and 10

6-Fluoro-2-(S)-(2-hydroxypropan-2-yl)-5-(1,2,3,4-tetrahydroisoquinolin-5-yl)-2,3,4,9-tetrahydro-1H-carbazole-8-carboxamide (Single Diastereomers)

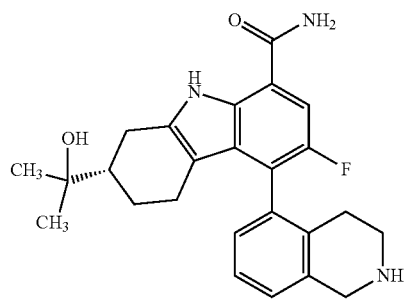

(I-9, I-10)

Crude 6-fluoro-2-(S)-(2-hydroxypropan-2-yl)-5-(RS)-(1,2,3,4-tetrahydroisoquinolin-5-yl)-2,3,4,9-tetrahydro-1H-carbazole-8-carboxamide (mixture of diastereomers) [Intermediate 8] was subjected to preparative reverse-phase HPLC. The first peak eluting from the column, after neutralization with saturated aqueous NaHCO₃, provided one diastereomer of 6-fluoro-2-(S)-(2-hydroxypropan-2-yl)-5-(1,2,3,4-tetrahydroisoquinolin-5-yl)-2,3,4,9-tetrahydro-1H-carbazole-8-carboxamide [Intermediate 9] (0.036 g, 25% yield), contaminated with 1-2% of the diastereomer in the second peak. The second peak eluting from the column, after neutralization with saturated aqueous NaHCO₃, provided the other diastereomer of 6-fluoro-2-(S)-(2-hydroxypropan-2-yl)-5-(1,2,3,4-tetrahydroisoquinolin-5-yl)-2,3,4,9-tetrahydro-1H-carbazole-8-carboxamide [Intermediate 10] (0.031 g, 20% yield), contaminated with 8% of the diastereomer in the first peak. The mass spectra for both diastereomers were the same as those for Intermediate 8. HPLC retention times (Column: CHROMOLITH® SpeedROD 4.6×50 mm; solvent: MeOH-water containing 0.1% TFA at 4.0 mL/min; gradient: 10-90% over 4 min): Intermediate 9-1.88 min; Intermediate 10-2.02 min. The absolute configurations about the atropisomeric bond were not assigned.

Intermediate 11

(RS)-3-Fluoro-4-(1,2,3,4-tetrahydroisoquinolin-5-yl)-9H-carbazole-1-carboxamide

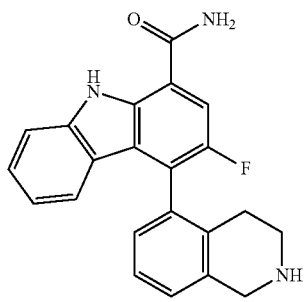

(I-11)

Following the procedures used to prepare Intermediate 8, 4-bromo-3-fluoro-9H-carbazole-1-carboxamide [Intermediate 3] was converted into (RS)-3-fluoro-4-(1,2,3,4-tetrahydroisoquinolin-5-yl)-9H-carbazole-1-carboxamide. Mass spectrum m/z 360 (M+H)⁺. ¹H NMR (400 MHz, MeOH-d₄) δ 7.85 (d, J=10.4 Hz, 1H), 7.60 (d, J=8.2 Hz, 1H), 7.53-7.46 (m, 1H), 7.45-7.41 (m, 1H), 7.40-7.36 (m, 1H), 7.36-7.30 (m, 1H), 6.93-6.86 (m, 1H), 6.85-6.78 (m, 1H), 4.50-4.27 (m, 2H), 3.30-3.07 (m, 2H), 2.85-2.68 (m, 1H), 2.62-2.43 (m, 1H).

Intermediate 12

(RS)-3,3,6-Trifluoro-5-(1,2,3,4-tetrahydroisoquinolin-5-yl)-2,3,4,9-tetrahydro-1H-carbazole-8-carboxamide

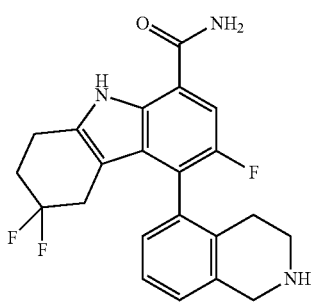

(I-12)

Following the procedures used to prepare Intermediate 8, 5-bromo-3,3,6-trifluoro-2,3,4,9-tetrahydro-1H-carbazole-8-carboxamide [Intermediate 2] was converted into (RS)-3,3,6-trifluoro-5-(1,2,3,4-tetrahydroisoquinolin-5-yl)-2,3,4,9-tetrahydro-1H-carbazole-8-carboxamide. Mass spectrum m/z 400 (M+H)⁺. ¹H NMR (400 MHz, CDCl₃) δ 10.10 (br. s., 1H), 7.34-7.29 (m, 1H), 7.27-7.23 (m, 1H), 7.20 (d, J=9.8 Hz, 1H), 7.15 (dd, J=7.4, 1.3 Hz, 1H), 4.81-4.55 (m, 2H), 3.75-3.59 (m, 1H), 3.47 (ddd, J=12.8, 7.9, 4.6 Hz, 1H), 3.01 (t, J=6.6 Hz, 2H), 2.68-2.17 (m, 6H).

Intermediate 13

(RS)-3-Fluoro-4-(1,2,3,4-tetrahydroisoquinolin-5-yl)-7-(trifluoromethyl)-9H-carbazole-1-carboxamide TFA Salt

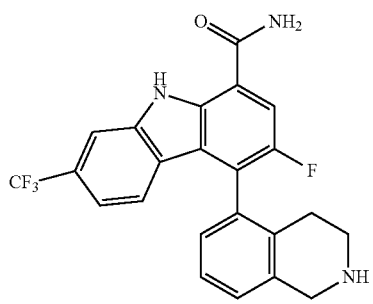

(I-13)

Following the procedures used to prepare Intermediate 8, 4-bromo-3-fluoro-7-(trifluoromethyl)-9H-carbazole-1-carboxamide [Intermediate 4] was converted into (RS)-3-fluoro-4-(1,2,3,4-tetrahydroisoquinolin-5-yl)-7-(trifluoromethyl)-9H-carbazole-1-carboxamide TFA salt. Mass spectrum m/z 428 (M+H)⁺, 469 (M+H+CH₃CN)⁺.

Intermediate 14

6-Fluoro-5-(1,2,3,4-tetrahydroisoquinolin-5-yl)-2-(trifluoromethyl)-2,3,4,9-tetrahydro-1H-carbazole-8-carboxamide TFA Salt (Mixture of Diastereomers)

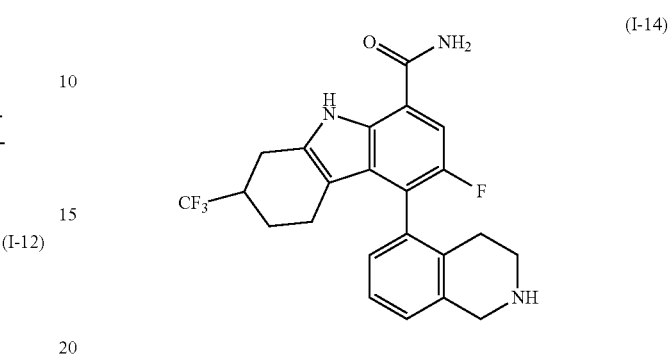

(I-14)

Following the procedures used to prepare Intermediate 8, (RS)-5-bromo-6-fluoro-2-(trifluoromethyl)-2,3,4,9-tetrahydro-1H-carbazole-8-carboxamide [Intermediate 1] was converted into (RS)-3-fluoro-4-(1,2,3,4-tetrahydroisoquinolin-5-yl)-7-(trifluoromethyl)-9H-carbazole-1-carboxamide TFA salt, as a mixture of diastereomers. Mass spectrum m/z 432 (M+H)⁺, 473 (M+H+CH₃CN)⁺.

Intermediate 15

(RS)-4-(3,4-Dihydro-2H-benzo[b][1,4]oxazin-8-yl)-3-fluoro-9H-carbazole-1-carboxamide

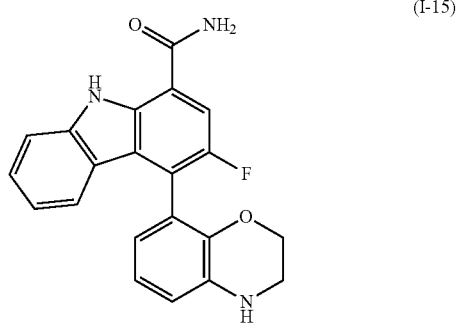 [SMILES: NC(=O)c1cc(F)c(-c2cccc3c2OCCN3)c2c1[nH]c1ccccc12]

(I-15)

Intermediate 15A: tert-Butyl 8-bromo-2H-benzo[b][1,4]oxazine-4(3H)-carboxylate

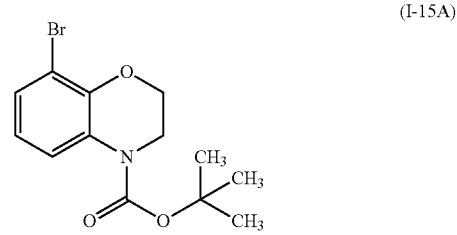 [SMILES: CC(C)(C)OC(=O)N1CCOc2c(Br)cccc21]

(I-15A)

A solution of 8-bromo-3,4-dihydro-2H-benzo[b][1,4]oxazine [prepared according to procedures described in Example 10 of PCT Publication No. WO 2012/149236]

(1.20 g, 5.61 mmol), di-tert-butyl dicarbonate (1.43 mL, 6.17 mmol) and triethylamine (2.34 mL, 16.8 mmol) in THF (20 mL) was stirred at room temperature for 5 h. No reaction was observed so the mixture was concentrated. The residue was dissolved in 1,4-dioxane (25 mL), treated with $K_2CO_3$ (0.775 g, 5.61 mmol) and additional di-tert-butyl dicarbonate (1.43 mL, 6.17 mmol), and the mixture was heated at 90° C. for 3 days. The mixture was filtered and the filtrate was concentrated. The residue was purified by column chromatography on silica gel, eluting with EtOAc-hexanes (gradient from 0-50%), to provide tert-butyl 8-bromo-2H-benzo[b][1,4]oxazine-4(3H)-carboxylate as a light brown oil (1.37 g, 78% yield). $^1$H NMR (400 MHz, $CDCl_3$) δ 7.75 (d, J=7.5 Hz, 1H), 7.27 (dd, J=8.0, 1.5 Hz, 1H), 6.78 (t, J=8.2 Hz, 1H), 4.38 (dd, J=5.1, 4.2 Hz, 2H), 3.92-3.87 (m, 2H), 1.56 (s, 9H).

Intermediate 15

Following the procedures used to prepare Intermediate 8, but substituting 4-bromo-3-fluoro-9H-carbazole-1-carboxamide [Intermediate 3] for (S)-5-bromo-6-fluoro-2-(2-hydroxypropan-2-yl)-2,3,4,9-tetrahydro-1H-carbazole-8-carboxamide [Intermediate 7] in Step B, tert-butyl 8-bromo-2H-benzo[b][1,4]oxazine-4(3H)-carboxylate was converted into (RS)-4-(3,4-dihydro-2H-benzo[b][1,4]oxazin-8-yl)-3-fluoro-9H-carbazole-1-carboxamide. Mass spectrum m/z 362 (M+H)$^+$. $^1$H NMR (400 MHz, MeOH-d$_4$) δ 7.76 (d, J=10.4 Hz, 1H), 7.56 (d, J=8.2 Hz, 1H), 7.35 (ddd, J=8.2, 7.1, 1.2 Hz, 1H), 7.24-7.18 (m, 1H), 6.98-6.89 (m, 2H), 6.87-6.81 (m, 1H), 6.67 (dd, J=7.3, 1.6 Hz, 1H), 4.16-3.96 (m, 2H), 3.43-3.34 (m, 2H).

Intermediate 16

(RS)-3-Fluoro-4-(2,3,4,5-tetrahydrobenzo[b][1,4]oxazepin-9-yl)-7-(trifluoromethyl)-9H-carbazole-1-carboxamide TFA Salt

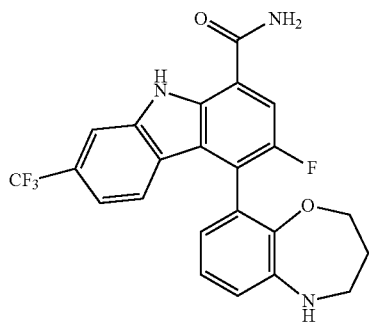

(I-16)

Following the procedures used to prepare Intermediate 8 but substituting tert-butyl 9-bromo-3,4-dihydrobenzo[b][1,4]oxazepine-5(2H)-carboxylate [prepared according to the procedure described for Intermediate D53 of PCT Publication No. WO 2012/170752] for tert-butyl 5-bromo-3,4-dihydroisoquinoline-2(1H)-carboxylate, 4-bromo-3-fluoro-7-(trifluoromethyl)-9H-carbazole-1-carboxamide [Intermediate 4] was converted into (RS)-3-fluoro-4-(2,3,4,5-tetrahydrobenzo[b][1,4]oxazepin-9-yl)-7-(trifluoromethyl)-9H-carbazole-1-carboxamide as the TFA salt. Mass spectrum m/z 444 (M+H)$^+$.

Intermediate 17

3-Fluoro-4-(4,4,5,5-tetramethyl-1,3,2-dioxaborolan-2-yl)-9H-carbazole-1-carboxamide

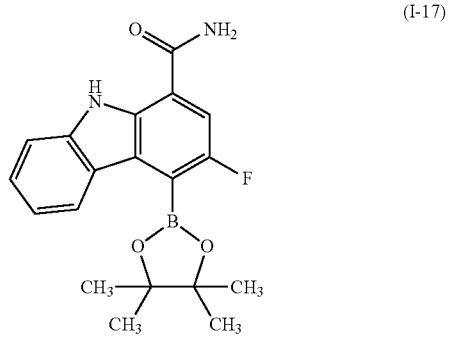 [SMILES: CC1(C)OB(c2c(F)cc(C(N)=O)c3[nH]c4ccccc4c23)OC1(C)C]

(I-17)

Following the procedures used to prepare Intermediate 15, 4-bromo-3-fluoro-9H-carbazole-1-carboxamide [Intermediate 3] was converted into 3-fluoro-4-(4,4,5,5-tetramethyl-1,3,2-dioxaborolan-2-yl)-9H-carbazole-1-carboxamide as a yellow glassy solid in 12% yield. Mass spectrum m/z 355 (M+H)$^+$. $^1$H NMR (400 MHz, $CDCl_3$) δ 8.56 (d, J=8.1 Hz, 1H), 7.58-7.48 (m, 2H), 7.37-7.20 (m, 2H), 1.56 (s, 12H).

Intermediate 18

(RS)-4-(3,4-Dihydro-2H-benzo[b][1,4]thiazin-8-yl)-3-fluoro-9H-carbazole-1-carboxamide TFA Salt

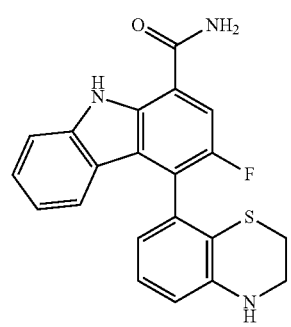

(I-18)

Intermediate 18A: tert-Butyl 8-bromo-2H-benzo[b][1,4]thiazine-4(3H)-carboxylate

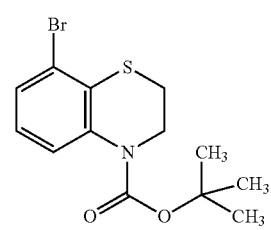

(I-18A)

Following the procedure used to prepare Intermediate 15A, 8-bromo-3,4-dihydro-2H-benzo[b][1,4]thiazine [prepared according to procedures described in Example 331 of PCT Publication No. WO 2012/149236] was converted into tert-butyl 8-bromo-2H-benzo[b][1,4]thiazine-4(3H)-carboxylate as a brown oil in 65% yield. Mass spectrum m/z 274, 276 (M+H–C$_4$H$_8$)$^+$.

Intermediate 18

A mixture of 3-fluoro-4-(4,4,5,5-tetramethyl-1,3,2-dioxaborolan-2-yl)-9H-carbazole-1-carboxamide [Intermediate 17] (38 mg, 0.107 mmol), tert-butyl 8-bromo-2H-benzo[b][1,4]thiazine-4(3H)-carboxylate (37.2 mg, 0.113 mmol), K$_3$PO$_4$ (45.5 mg, 0.215 mmol), and 1,1'-bis(di-tert-butylphosphino)ferrocene palladium dichloride (3.5 mg, 5.36 μmol) in THF (1.5 mL) and water (0.2 mL) was purged with nitrogen and stirred at 60° C. overnight. The mixture was cooled to room temperature, filtered through CELITE® and concentrated. The residue was dissolved in DCM (2 mL), treated with TFA and the mixture was stirred at room temperature for 30 min. The mixture was concentrated and the residue was subjected to preparative reverse-phase HPLC (YMC C$_{18}$ column, 5 μm, 30×250 mm, eluting with acetonitrile-water containing 0.1% TFA, gradient from 10-100%) to provide (RS)-4-(3,4-dihydro-2H-benzo[b][1,4]thiazin-8-yl)-3-fluoro-9H-carbazole-1-carboxamide TFA salt (23.6 mg, 58% yield) as a brown solid. Mass spectrum m/z 378 (M+H)$^+$. $^1$H NMR (400 MHz, MeOH-d$_4$) δ 7.78 (d, J=10.3 Hz, 1H), 7.57 (d, J=8.3 Hz, 1H), 7.36 (ddd, J=8.3, 7.0, 1.3 Hz, 1H), 7.18 (t, J=7.8 Hz, 1H), 7.01-6.94 (m, 2H), 6.94-6.88 (m, 1H), 6.84 (d, J=7.5 Hz, 1H), 3.70-3.57 (m, 2H), 3.07-2.88 (m, 2H).

Example 1

(RS)-5-(2-Acryloyl-1,2,3,4-tetrahydroisoquinolin-5-yl)-3,3,6-trifluoro-2,3,4,9-tetrahydro-1H-carbazole-8-carboxamide

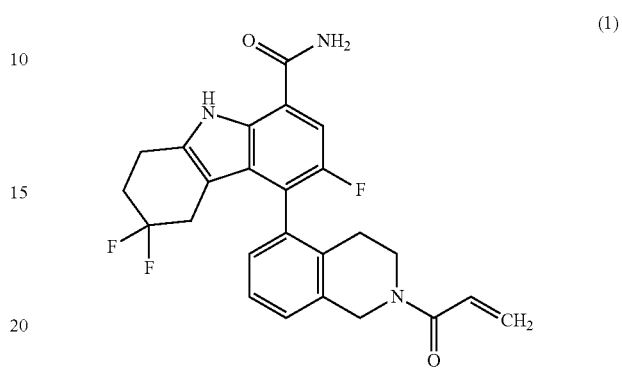

(1)

A mixture of 3,3,6-trifluoro-5-(1,2,3,4-tetrahydroisoquinolin-5-yl)-2,3,4,9-tetrahydro-1H-carbazole-8-carboxamide [Intermediate 12] (47 mg, 0.118 mmol) and DIEA (62 μL, 0.353 mmol) in 3:1 DCM-THF (0.5 mL), was treated at 0° C. with acryloyl chloride (11 μl, 0.129 mmol). After stirring for 10 min, the mixture was diluted with DCM, washed with water, dried and concentrated. The residue was triturated with EtOAc to provide (RS)-5-(2-acryloyl-1,2,3,4-tetrahydroisoquinolin-5-yl)-3,3,6-trifluoro-2,3,4,9-tetrahydro-1H-carbazole-8-carboxamide as a white solid (47 mg, 84% yield). Mass spectrum m/z 454 (M+H)$^+$. $^1$H NMR (500 MHz, DMSO-d$_6$) δ 11.20 (s, 1H), 8.14 (br. s., 1H), 7.62 (d, J=10.7 Hz, 1H), 7.55 (br. s., 1H), 7.42-7.26 (m, 2H), 7.19-7.11 (m, 1H), 7.00-6.70 (m, 1H), 6.14 (d, J=16.6 Hz, 1H), 5.88-5.62 (m, 1H), 4.95-4.66 (m, 2H), 3.80-3.48 (m, 2H), 2.94 (t, J=5.5 Hz, 2H), 2.48-2.08 (m, 6H).

The Examples in Table 1 were prepared by the general procedure described for Example 1 or similar procedures, using the indicated starting material.

TABLE 1

| Example, Description | Structure | Starting Material | Mass Spectrum |
|---|---|---|---|
| 2 (racemate) | ![structure] | Intermediate 11 | m/z 414 (M + H)$^+$ |

TABLE 1-continued

| Example, Description | Structure | Starting Material | Mass Spectrum |
|---|---|---|---|
| 3 (racemate) | 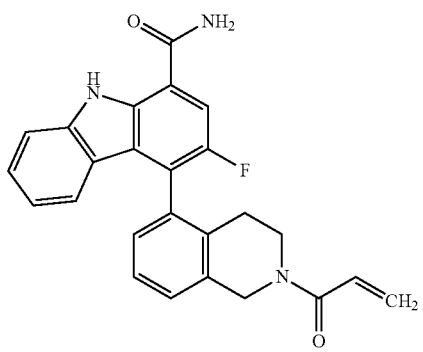 | Intermediate 15 | m/z 416 (M + H)+ |
| 4 (racemate) | 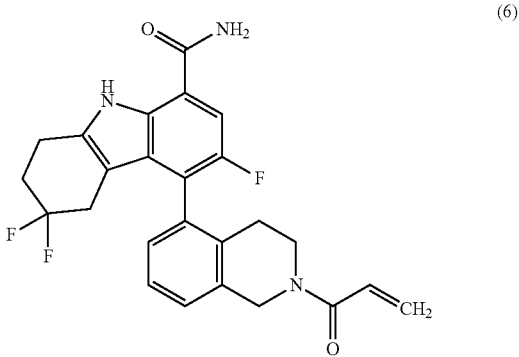 | Intermediate 13 | m/z 482 (M + H)+ |

Example 5

4-(2-Acryloyl-1,2,3,4-tetrahydroisoquinolin-5-yl)-3-fluoro-9H-carbazole-1-carboxamide (Single Enantiomeric Atropisomer)

(5)

A sample of (RS)-4-(2-acryloyl-1,2,3,4-tetrahydroisoquinolin-5-yl)-3-fluoro-9H-carbazole-1-carboxamide [Example 2] (13 mg) was separated by chiral super-critical fluid chromatography (Column: CHIRALCEL® AS-H (3×25 cm, 5 μm); Mobile Phase: $CO_2$-MeOH (70:30) at 150 mL/min, 100 bars, 35° C.; sample preparation: 3 mg/mL in MeOH; injection: 1.5 mL). The first peak eluting from the column provided one enantiomeric atropisomer of 4-(2-acryloyl-1,2,3,4-tetrahydroisoquinolin-5-yl)-3-fluoro-9H-carbazole-1-carboxamide [Example 5] (5.2 mg). Mass spectrum m/z 414 (M+H)+. $^1$H NMR (400 MHz, DMSO-$d_6$) δ 11.55 (s, 1H), 8.25 (br. s., 1H), 7.99 (d, J=10.6 Hz, 1H), 7.74 (d, J=8.2 Hz, 1H), 7.66 (br. s., 1H), 7.53-7.39 (m, 2H), 7.38-7.17 (m, 2H), 7.08-6.54 (m, 3H), 6.28-6.01 (m, 1H), 5.83-5.54 (m, 1H), 5.12-4.69 (m, 2H), 3.89-3.41 (m, 2H), 2.71-2.28 (m, 2H, buried under residual DMSO peak). The absolute configuration of Example 5 has not been assigned.

Example 6

5-(2-Acryloyl-1,2,3,4-tetrahydroisoquinolin-5-yl)-3,3,6-trifluoro-2,3,4,9-tetrahydro-1H-carbazole-8-carboxamide (Single Enantiomeric Atropisomer)

(6)

A sample of (RS)-5-(2-acryloyl-1,2,3,4-tetrahydroisoquinolin-5-yl)-3,3,6-trifluoro-2,3,4,9-tetrahydro-1H-carbazole- 8-carboxamide [Example 1] (42 mg) was separated by chiral super-critical fluid chromatography (Column: CHIRALCEL® AS-H (3×25 cm, 5 μm); Mobile Phase: CO$_2$-MeOH (65-35) at 150 mL/min, 100 bars, 35° C.; sample preparation: 7 mg/mL in MeOH-DMF (9:1); injection: 1.75 mL). The first peak eluting from the column provided one enantiomeric atropisomer of 5-(2-acryloyl-1,2,3,4-tetrahydroisoquinolin-5-yl)-3,3,6-trifluoro-2,3,4,9-tetrahydro-1H-carbazole-8-carboxamide [Example 6] (5 mg). Mass spectrum m/z 454 (M+H)$^+$. $^1$H NMR (400 MHz, MeOH-d$_4$) δ 7.50 (d, J=10.6 Hz, 1H), 7.41-7.31 (m, 2H), 7.19 (d, J=3.3 Hz, 1H), 6.97-6.70 (m, 1H), 6.25 (dd, J=16.7, 1.8 Hz, 1H), 5.84-5.70 (m, 1H), 4.98-4.86 (m, 2H), 3.93-3.78 (m, 1H), 3.78-3.53 (m, 1H), 3.09-2.93 (m, 2H), 2.73-2.34 (m, 3H), 2.30-2.07 (m, 3H). The absolute configuration of Example 6 has not been assigned.

Example 7

4-(2-Acryloyl-1,2,3,4-tetrahydroisoquinolin-5-yl)-3-fluoro-7-(trifluoromethyl)-9H-carbazole-1-carboxamide (Single Enantiomeric Atropisomer)

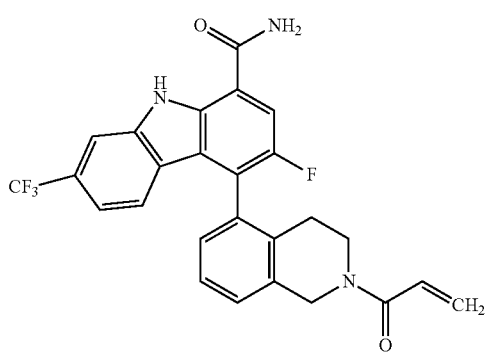 [SMILES: C=CC(=O)N1CCc2c(cccc2-c2c(F)cc(C(N)=O)c3[nH]c4cc(C(F)(F)F)ccc4c23)C1]

(7)

A sample of (RS)-4-(2-acryloyl-1,2,3,4-tetrahydroisoquinolin-5-yl)-3-fluoro-7-(trifluoromethyl)-9H-carbazole-1-carboxamide [Example 4] (20 mg) was separated by chiral super-critical fluid chromatography (Column: IC (3×25 cm, 5 μm); Mobile Phase: CO$_2$-MeOH (60:40) at 140 mL/min, 100 bar, 30° C.; sample preparation: 2.5 mg/mL in MeOH; injection: 1.7 mL). The second peak eluting from the column provided one enantiomeric atropisomer of 4-(2-acryloyl-1,2,3,4-tetrahydroisoquinolin-5-yl)-3-fluoro-7-(trifluoromethyl)-9H-carbazole-1-carboxamide [Example 7] (5.8 mg). Mass spectrum m/z 482 (M+H)$^+$. $^1$H NMR (400 MHz, MeOH-d$_4$) δ 8.02-7.90 (m, 2H), 7.56-7.45 (m, 2H), 7.37-7.28 (m, 1H), 7.19-7.08 (m, 1H), 6.96-6.85 (m, 1H), 6.71 (dd, J=16.7, 10.7 Hz, 1H), 6.24 (t, J=15.7 Hz, 1H), 5.88-5.63 (m, 1H), 5.06-4.92 (m, 2H), 3.80 (td, J=12.4, 5.6 Hz, 1H), 3.72-3.55 (m, 1H), 2.74-2.57 (m, 1H), 2.56-2.35 (m, 1H). The absolute configuration of Example 7 has not been assigned.

Example 8

4-(4-Acryloyl-3,4-dihydro-2H-benzo[b][1,4]oxazin-8-yl)-3-fluoro-9H-carbazole-1-carboxamide (Single Enantiomeric Atropisomer)

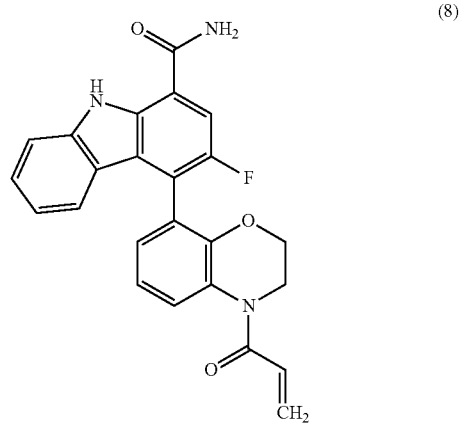 [SMILES: C=CC(=O)N1CCOc2c(-c3c(F)cc(C(N)=O)c4[nH]c5ccccc5c34)cccc21]

(8)

A sample of (RS)-4-(4-acryloyl-3,4-dihydro-2H-benzo[b][1,4]oxazin-8-yl)-3-fluoro-9H-carbazole-1-carboxamide [Example 3] (76 mg) was separated by chiral super-critical fluid chromatography (Column: CHIRALPAK® IC 3×25 cm; 5 μM; Mobile Phase: CO$_2$-MeOH (55:45) at 140 mL/min, 30° C.; sample preparation: dissolved in 1:1 MeOH-DCM; injection: 2.0 mL). The first peak eluting from the column provided one enantiomeric atropisomer of 4-(4-acryloyl-3,4-dihydro-2H-benzo[b][1,4]oxazin-8-yl)-3-fluoro-9H-carbazole-1-carboxamide [Example 8] (31.1 mg). Mass spectrum m/z 416 (M+H)$^+$. $^1$H NMR (400 MHz, MeOH-d$_4$) δ 7.80 (d, J=10.5 Hz, 1H), 7.59 (m, 2H), 7.37 (ddd, J=8.2, 7.1, 1.2 Hz, 1H), 7.27 (dd, J=7.6, 1.6 Hz, 1H), 7.20-7.14 (m, 1H), 7.11 (d, J=7.9 Hz, 1H), 7.02-6.91 (m, 2H), 6.47 (dd, J=16.8, 1.8 Hz, 1H), 5.97-5.89 (m, 1H), 4.28-4.07 (m, 4H). The absolute configuration of Example 8 has not been assigned.

Example 9

5-(2-Acryloyl-1,2,3,4-tetrahydroisoquinolin-5-yl)-6-fluoro-2-(S)-(2-hydroxypropan-2-yl)-2,3,4,9-tetrahydro-1H-carbazole-8-carboxamide (Single Diastereomer)

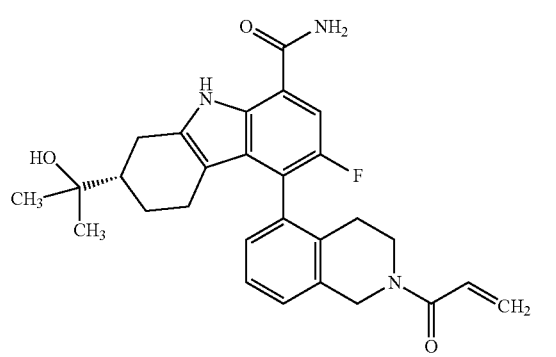

(9)

A mixture of a single diastereomer of 6-fluoro-2-(S)-(2-hydroxypropan-2-yl)-5-(1,2,3,4-tetrahydroisoquinolin-5-yl)-2,3,4,9-tetrahydro-1H-carbazole-8-carboxamide [Intermediate 9] (0.036 g, 0.085 mmol) and DIEA (0.060 mL, 0.342 mmol) in THF (2 mL) at room temperature was treated with acryloyl chloride (6.9 μL, 0.085 mmol). The mixture was stirred for 30 min, diluted with EtOAc, washed sequentially with water and saturated brine, dried and concentrated. The residue was purified by column chromatography on silica gel, eluting with EtOAc-hexanes (gradient from 50-75%). The resulting material was further purified by chiral super-critical fluid chromatography (Column: CHIRALPAK® AS-H (3×25 cm, 5 μm); Mobile Phase: $CO_2$-MeOH (65:35) at 150 mL/min, 35° C.). The second peak eluting from the column provided a single diastereomer of 5-(2-acryloyl-1,2,3,4-tetrahydroisoquinolin-5-yl)-6-fluoro-2-(S)-(2-hydroxypropan-2-yl)-2,3,4,9-tetrahydro-1H-carbazole-8-carboxamide as a white solid (0.030 g, 73% yield). Mass spectrum m/z 476 (M+H)$^+$. The absolute configuration about the atropisomeric bond was not determined.

Examples 10 and 11

5-(2-Acryloyl-1,2,3,4-tetrahydroisoquinolin-5-yl)-6-fluoro-2-(trifluoromethyl)-2,3,4,9-tetrahydro-1H-carbazole-8-carboxamide, Single Homochiral Diastereomers

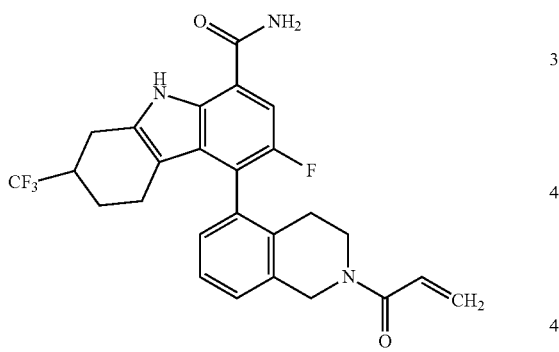

(10 and 11)

Following the procedure used to prepare Example 1, 6-fluoro-5-(1,2,3,4-tetrahydroisoquinolin-5-yl)-2-(trifluoromethyl)-2,3,4,9-tetrahydro-1H-carbazole-8-carboxamide TFA salt (mixture of diastereomers) [Intermediate 14] was converted into 5-(2-acryloyl-1,2,3,4-tetrahydroisoquinolin-5-yl)-6-fluoro-2-(trifluoromethyl)-2,3,4,9-tetrahydro-1H-carbazole-8-carboxamide, as a mixture of four diastereomers, in 49% yield. Mass spectrum m/z 486 (M+H)$^+$.

A sample of this material (107 mg) was separated by chiral super-critical fluid chromatography (Column: Chiral IC (3×25 cm, 5 μm); Mobile Phase: $CO_2$-MeOH (70:30) at 85 mL/min; sample preparation: 10.7 mg/mL in MeOH; injection: 1.0 mL). The third peak eluting from the column provided one homochiral diastereomer of 5-(2-acryloyl-1,2,3,4-tetrahydroisoquinolin-5-yl)-6-fluoro-2-(trifluoromethyl)-2,3,4,9-tetrahydro-1H-carbazole-8-carboxamide [Example 10] (14.5 mg). $^1$H NMR (400 MHz, MeOH-d$_4$) δ 7.49 (d, J=10.4 Hz, 1H), 7.38-7.28 (m, 2H), 7.24-7.13 (m, 1H), 6.99-6.68 (m, 1H), 6.26 (dd, J=16.8, 1.8 Hz, 1H), 5.87-5.71 (m, 1H), 4.93-4.87 (m, 2H), 3.77 (quin, J=6.2 Hz, 2H), 3.08 (dd, J=16.4, 4.6 Hz, 1H), 2.83 (dd, J=16.3, 11.4 Hz, 1H), 2.67-2.40 (m, 3H), 2.08-1.86 (m, 3H), 1.66-1.43 (m, 1H).

The fourth peak eluting from the column provided a second homochiral diastereomer of 5-(2-acryloyl-1,2,3,4-tetrahydroisoquinolin-5-yl)-6-fluoro-2-(trifluoromethyl)-2,3,4,9-tetrahydro-1H-carbazole-8-carboxamide [Example 11] (21.2 mg), contaminated with about 2% of the homochiral diastereomer which eluted as the third peak [Example 10]. $^1$H NMR (400 MHz, MeOH-d$_4$) δ 7.48 (d, J=10.5 Hz, 1H), 7.36-7.27 (m, 2H), 7.19-7.11 (m, 1H), 6.98-6.70 (m, 1H), 6.26 (d, J=16.8 Hz, 1H), 5.86-5.68 (m, 1H), 4.99-4.75 (m, 2H), 3.96-3.56 (m, 2H), 3.09 (dd, J=16.5, 5.3 Hz, 1H), 2.90-2.75 (m, 1H), 2.74-2.33 (m, 3H), 2.24-2.07 (m, 1H), 1.95 (dd, J=15.2, 2.9 Hz, 1H), 1.82 (d, J=16.0 Hz, 1H), 1.49 (qd, J=12.2, 5.2 Hz, 1H).

The mass spectra of both homochiral diastereomers were the same as that of the mixture: m/z 486 (M+H)$^+$. The absolute configurations of Examples 10 and 11 have not been assigned.

Example 12

4-(5-Acryloyl-2,3,4,5-tetrahydrobenzo[b][1,4]oxazepin-9-yl)-3-fluoro-7-(trifluoromethyl)-9H-carbazole-1-carboxamide (Single Enantiomeric Atropisomer)

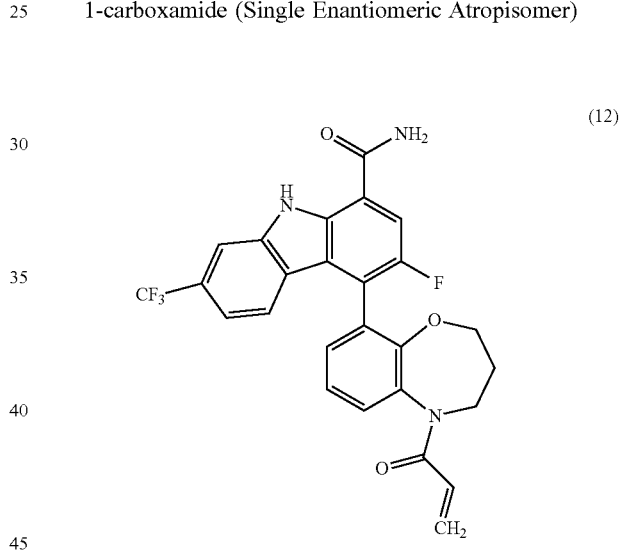

(12)

Following the procedure used to prepare Example 1, (RS)-3-fluoro-4-(2,3,4,5-tetrahydrobenzo[b][1,4]oxazepin-9-yl)-7-(trifluoromethyl)-9H-carbazole-1-carboxamide TFA salt [Intermediate 16] was converted into (RS)-4-(5-acryloyl-2,3,4,5-tetrahydrobenzo[b][1,4]oxazepin-9-yl)-3-fluoro-7-(trifluoromethyl)-9H-carbazole-1-carboxamide in 77% yield. Mass spectrum m/z 498 (M+H)$^+$.

A sample of this material (63 mg) was purified by chiral super-critical fluid chromatography (Column: CHIRALPAK® OJ-H (3×25 cm, 5 m); Mobile Phase: $CO_2$-MeOH (80:20) at 85 mL/min; sample preparation: 15.75 mg/mL in MeOH; injection: 2.0 mL). The second peak eluting from the column provided a single enantiomeric atropisomer of 4-(5-acryloyl-2,3,4,5-tetrahydrobenzo[b][1,4]oxazepin-9-yl)-3-fluoro-7-(trifluoromethyl)-9H-carbazole-1-carboxamide (21.3 mg). Mass spectrum m/z 498 (M+H)$^+$. $^1$H NMR (400 MHz, MeOH-d$_4$) δ 8.05-7.83 (m, 2H), 7.55-7.32 (m, 3H), 7.28-6.97 (m, 2H), 6.36 (m, 2H), 5.77 (br. s., 1H), 4.90 (br. s., 1H), 4.28-3.74 (m, 2H), 3.05 (br. s., 1H), 2.28-2.04 (m, 1H), 1.85 (br. s., 1H). The absolute configuration about the atropisomeric bond was not determined.

Additional Examples which were prepared by procedures described above, using the starting material(s) and procedures indicated, are shown in Table 2.

TABLE 2

| Example | Structure | Starting Materials | Procedures | Mass Spectrum |
|---|---|---|---|---|
| 13 (racemic) | 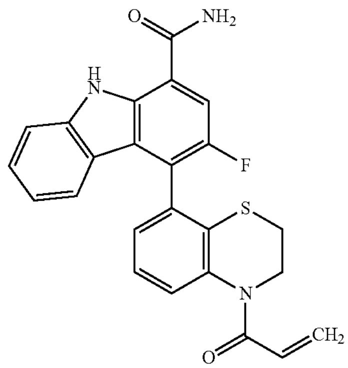 [SMILES: C=CC(=O)N1CCSc2c(-c3c(F)cc(C(N)=O)c4[nH]c5ccccc5c34)cccc21] | Intermediate 18 | (a) | m/z 432 (M + H)+ |
| 14 single enantiomer (peak 1) | 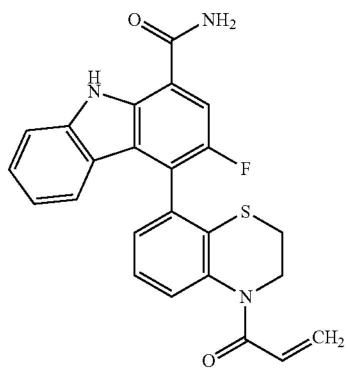 [SMILES: C=CC(=O)N1CCSc2c(-c3c(F)cc(C(N)=O)c4[nH]c5ccccc5c34)cccc21] | Example 13 | (b) | m/z 432 (M + H)+ |

(a) Prepared following the procedure used to prepare Example 1 or similar procedures.
(b) Prepared by super-critical fluid chromatography of the racemic compound. Absolute configuration was not assigned.

Comparative Example 15

4-(2-Acryloyl-1,2,3,4-tetrahydroisoquinolin-5-yl)-3-fluoro-9H-carbazole-1-carboxamide (Single Enantiomeric Atropisomer)

(15)

A second enantiomeric atropisomer of 4-(2-acryloyl-1,2,3,4-tetrahydroisoquinolin-5-yl)-3-fluoro-9H-carbazole-1-carboxamide was isolated from the second peak eluting from the column during the separation of Example 2 by chiral super-critical fluid chromatography to isolate Example 5, and provided Comparative Example 12 (6.1 mg). This material had the same mass spectrum and NMR spectrum as Example 5. The absolute configuration of Comparative Example 12 has not been determined.

Comparative Example 16

5-(2-Acryloyl-1,2,3,4-tetrahydroisoquinolin-5-yl)-3,3,6-trifluoro-2,3,4,9-tetrahydro-1H-carbazole-8-carboxamide (Single Enantiomeric Atropisomer)

(16)

A second enantiomeric atropisomer of 5-(2-acryloyl-1,2,3,4-tetrahydroisoquinolin-5-yl)-3,3,6-trifluoro-2,3,4,9-tetrahydro-1H-carbazole-8-carboxamide was isolated from the second peak eluting from the column during the separation of Example 1 by chiral super-critical fluid chromatography to isolate Example 6, and provided Comparative Example 13 (5 mg). This material had the same mass spectrum and NMR spectrum as Example 6. The absolute configuration of Comparative Example 13 has not been determined.

Comparative Example 17

4-(2-Acryloyl-1,2,3,4-tetrahydroisoquinolin-5-yl)-3-fluoro-7-(trifluoromethyl)-9H-carbazole-1-carboxamide (Single Enantiomeric Atropisomer)

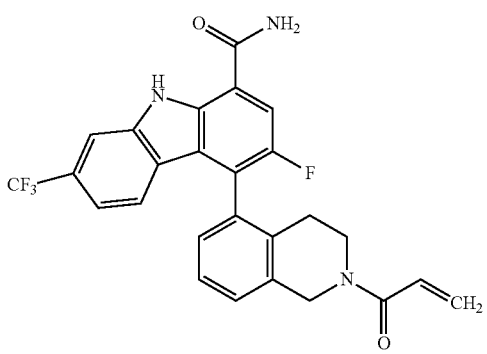

(17)

A second enantiomeric atropisomer of 4-(2-acryloyl-1,2,3,4-tetrahydroisoquinolin-5-yl)-3-fluoro-7-(trifluoromethyl)-9H-carbazole-1-carboxamide was isolated from the first peak eluting from the column during the separation of Example 4 by chiral super-critical fluid chromatography to isolate Example 7, and provided Comparative Example 14 (5.9 mg). This material had the same mass spectrum and NMR spectrum as Example 7. The absolute configuration of Comparative Example 14 has not been determined.

Comparative Example 18

4-(4-Acryloyl-3,4-dihydro-2H-benzo[b][1,4]oxazin-8-yl)-3-fluoro-9H-carbazole-1-carboxamide (Single Enantiomeric Atropisomer)

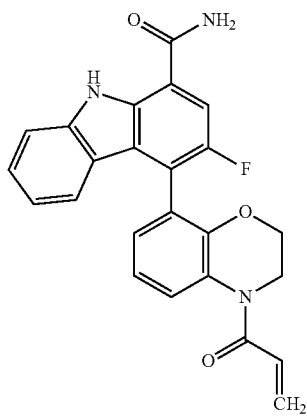

(18)

A second enantiomeric atropisomer of 4-(4-acryloyl-3,4-dihydro-2H-benzo[b][1,4]oxazin-8-yl)-3-fluoro-9H-carbazole-1-carboxamide was isolated from the second peak eluting from the column during the separation of Example 3 by chiral super-critical fluid chromatography to isolate Example 8, and provided Comparative Example 15 (32.1 mg). This material had the same mass spectrum and NMR spectrum as Example 8. The absolute configuration of Comparative Example 15 has not been determined.

Comparative Example 19

5-(2-Acryloyl-1,2,3,4-tetrahydroisoquinolin-5-yl)-6-fluoro-2-(S)-(2-hydroxypropan-2-yl)-2,3,4,9-tetrahydro-1H-carbazole-8-carboxamide (Single Diastereomer)

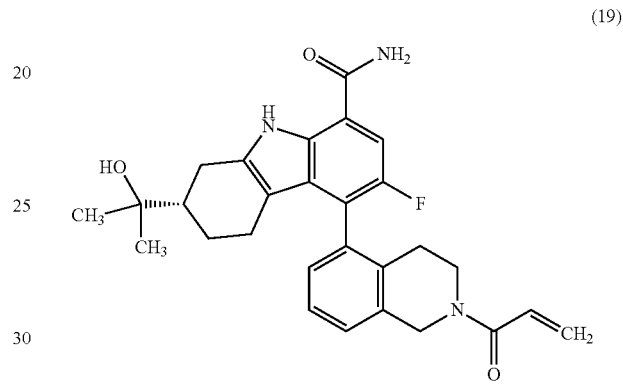

(19)

Following the procedure used to prepare Example 9 from Intermediate 10, the other diastereomer of 6-fluoro-2-(S)-(2-hydroxypropan-2-yl)-5-(1,2,3,4-tetrahydroisoquinolin-5-yl)-2,3,4,9-tetrahydro-1H-carbazole-8-carboxamide [Intermediate 11] was converted into a single diastereomer of 5-(2-acryloyl-1,2,3,4-tetrahydroisoquinolin-5-yl)-6-fluoro-2-(S)-(2-hydroxypropan-2-yl)-2,3,4,9-tetrahydro-1H-carbazole-8-carboxamide as a white solid in 76% yield. Mass spectrum m/z 476 (M+H)$^+$. The absolute configuration about the atropisomeric bond was not determined.

Comparative Examples 20 and 21

5-(2-Acryloyl-1,2,3,4-tetrahydroisoquinolin-5-yl)-6-fluoro-2-(trifluoromethyl)-2,3,4,9-tetrahydro-1H-carbazole-8-carboxamide, Single Homochiral Diastereomers

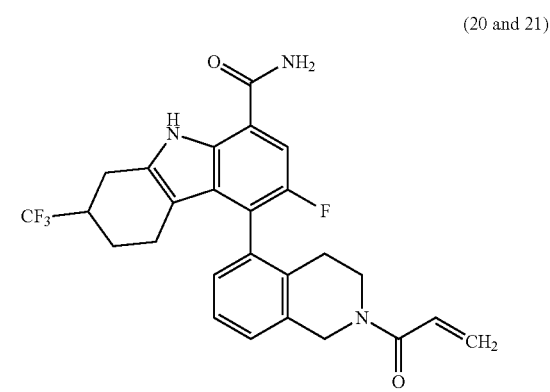 [SMILES: C=CC(=O)N1CCc2c(cccc2-c2c(F)cc(C(N)=O)c3[nH]c4c(c23)CCC(C(F)(F)F)C4)C1]

(20 and 21)

Two additional homochiral diastereomers of 5-(2-acryloyl-1,2,3,4-tetrahydroisoquinolin-5-yl)-6-fluoro-2-(trifluoromethyl)-2,3,4,9-tetrahydro-1H-carbazole-8-carboxamide were isolated during the separation of Examples 10 and 11 by chiral super-critical fluid chromatography. The first peak eluting from the column provided one homochiral diastereomer of 5-(2-acryloyl-1,2,3,4-tetrahydroisoquinolin-5-yl)-6-fluoro-2-(trifluoromethyl)-2,3,4,9-tetrahydro-1H-carbazole-8-carboxamide [Comparative Example 20] (15.0 mg). This material had the same NMR spectrum as Example 10, and therefore Example 10 and Comparative Example 20 are enantiomers.

The second peak eluting from the column provided another homochiral diastereomer of 5-(2-acryloyl-1,2,3,4-tetrahydroisoquinolin-5-yl)-6-fluoro-2-(trifluoromethyl)-2,3,4,9-tetrahydro-1H-carbazole-8-carboxamide [Comparative Example 21] (21.2 mg), contaminated with about 2% of the homochiral diastereomer which eluted as the first peak [Comparative Example 20]. This material had the same NMR spectrum as Example 11, and therefore Example 11 and Comparative Example 21 are enantiomers.

The mass spectra of both homochiral diastereomers was the same as that of the mixture: m/z 486 (M+H)$^+$. The absolute configurations of Comparative Examples 10 and 21 have not been determined.

Comparative Example 22

4-(5-Acryloyl-2,3,4,5-tetrahydrobenzo[b][1,4]oxazepin-9-yl)-3-fluoro-7-(trifluoromethyl)-9H-carbazole-1-carboxamide (Single Enantiomeric Atropisomer)

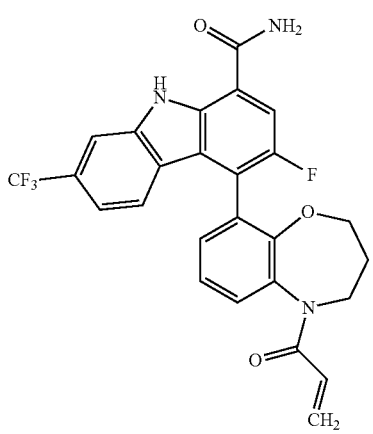

(22)

A second enantiomeric atropisomer of 4-(5-acryloyl-2,3,4,5-tetrahydrobenzo[b][1,4]oxazepin-9-yl)-3-fluoro-7-(trifluoromethyl)-9H-carbazole-1-carboxamide was isolated from the first peak eluting from the column during the isolation of Example 12 by chiral super-critical fluid chromatography, and provided Comparative Example 22 (20.5 mg). This material had the same mass spectrum and NMR spectrum as Example 12. The absolute configuration of Comparative Example 22 has not been determined.

Comparative Example 23

4-(4-Acryloyl-3,4-dihydro-2H-benzo[b][1,4]thiazin-8-yl)-3-fluoro-9H-carbazole-1-carboxamide (Single Enantiomeric Atropisomer)

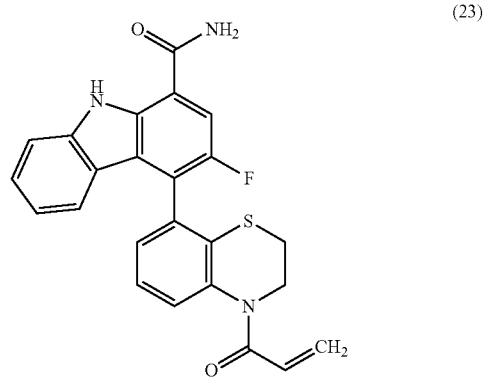 [SMILES: C=CC(=O)N1CCSc2c(-c3c(F)cc(C(N)=O)c4[nH]c5ccccc5c34)cccc21]

(23)

A second enantiomeric atropisomer of 4-(4-acryloyl-3,4-dihydro-2H-benzo[b][1,4]thiazin-8-yl)-3-fluoro-9H-carbazole-1-carboxamide was isolated from the second peak eluting from the column during the isolation of Example 14 by chiral super-critical fluid chromatography, and provided Comparative Example 23. This material had the same mass spectrum and NMR spectrum as Example 14. The absolute configuration of Comparative Example 23 has not been determined.

Example 24

4-(2-Acryloyl-1,2,3,4-tetrahydroisoquinolin-5-yl)-3-chloro-9H-carbazole-1-carboxamide, atropisomer 1

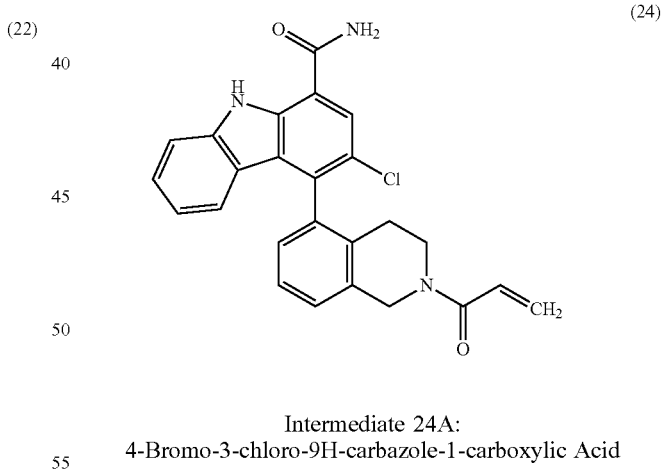

(24)

Intermediate 24A:
4-Bromo-3-chloro-9H-carbazole-1-carboxylic Acid

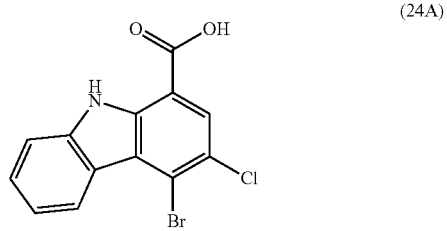

(24A)

To a solution of 5-bromo-6-chloro-2,3,4,9-tetrahydro-1H-carbazole-8-carboxylic acid, (793 mg, 2.413 mmol) in THF (30 mL) was added DDQ (1096 mg, 4.83 mmol), the mixture was stirred at 60° C. for 18 hour. The mixture was concentrated. The crude product was subjected to ISCO flash chromatography (silica gel/DCM:MeOH:HOAc 93.5: 5:1.5). Yield 4-bromo-3-chloro-9H-carbazole-1-carboxylic acid (350 mg, 1.024 mmol, 42.5% yield) as brown solid. LCMS: 1.19 min, M+H 324.

Intermediate 24B:
4-Bromo-3-chloro-9H-carbazole-1-carboxamide

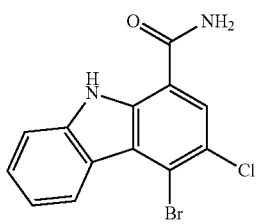

(24B)

A mixture of 4-bromo-3-chloro-9H-carbazole-1-carboxylic acid (350 mg, 1.078 mmol), ammonium chloride (288 mg, 5.39 mmol), BOP (525 mg, 1.186 mmol) and TEA (1.503 mL, 10.78 mmol) in DMF (5.0 mL) was stirred at room temperature for 60 min. The mixture was diluted with EtOAc (15 mL) and was washed with a solution of aqueous 1.0 M HCl (2×15 mL). The ethyl acetate layer was dried over sodium sulfate and concentrated. Crude yield: 4-bromo-3-chloro-9H-carbazole-1-carboxamide (203 mg, 0.596 mmol, 55.3% yield) as brown solid. $^1$H NMR (400 MHz, methanol-$d_4$) δ 8.77 (d, J=8.2 Hz, 1H), 8.08 (s, 1H), 7.71-7.62 (m, 1H), 7.60-7.49 (m, 1H), 7.30 (ddd, J=8.2, 7.2, 1.0 Hz, 1H).

Intermediate 24C: tert-Butyl 5-(1-carbamoyl-3-chloro-9H-carbazol-4-yl)-3,4-dihydroisoquinoline-2(1H)-carboxylate

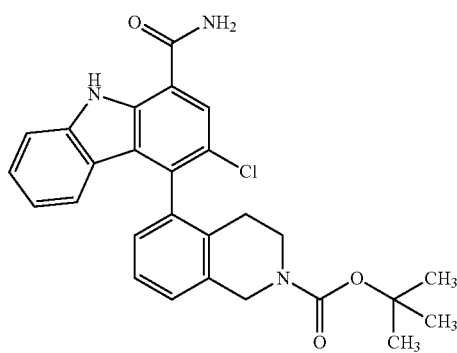

(24C)

A mixture of 4-bromo-3-chloro-9H-carbazole-1-carboxamide (80 mg, 0.247 mmol), tert-butyl 5-(4,4,5,5-tetramethyl-1,3,2-dioxaborolan-2-yl)-3,4-dihydroisoquinoline-2(1H)-carboxylate (89 mg, 0.247 mmol), 1,1'-bis(di-tert-butylphosphino)ferrocene palladium dichloride (8.06 mg, 0.012 mmol) and 2.0 M aqueous potassium phosphate tribasic (0.618 mL, 1.236 mmol) in dioxane (4.0 mL) was stirred at 60° C. in a seal vial under nitrogen for 18 hour. The mixture was diluted with EtOAc (15 mL) and was washed with a solution of aqueous saturated sodium bicarbonate (2×15 mL) and aqueous 1.0 M HCl (15 mL). The ethyl acetate layer was dried over sodium sulfate and concentrated. The crude product was subjected to ISCO flash chromatography (silica gel/DCM-EtOAc 100:0 to 0:100 gradient). Yield tert-butyl 5-(1-carbamoyl-3-chloro-9H-carbazol-4-yl)-3,4-dihydroisoquinoline-2(1H)-carboxylate (90 mg, 0.180 mmol, 72.7% yield) as white foam. LCMS: 1.21 min, 2M+H 324.

Example 24

To a solution of tert-butyl 5-(1-carbamoyl-3-chloro-9H-carbazol-4-yl)-3,4-dihydroisoquinoline-2(1H)-carboxylate (70 mg, 0.147 mmol) in DCM (1.0 mL) was added TFA (1.0 mL), the mixture was stirred at room temperature for 30 min. The mixture was concentrated to give crude 3-chloro-4-(1,2,3,4-tetrahydroisoquinolin-5-yl)-9H-carbazole-1-carboxamide, TFA salt.

To a solution of the 3-chloro-4-(1,2,3,4-tetrahydroisoquinolin-5-yl)-9H-carbazole-1-carboxamide, TFA salt and TEA (0.102 mL, 0.735 mmol) in DCM (1.0 mL) was added a solution of acryloyl chloride (0.013 mL, 0.162 mmol) in DCM (0.5 mL) at 0° C., the mixture was stirred at room temperature for 30 min. The crude product was subjected to ISCO flash chromatography (silica gel/hexane-EtOAc 100:0 to 0:100 gradient) to yield 4-(2-acryloyl-1,2,3,4-tetrahydroisoquinolin-5-yl)-3-chloro-9H-carbazole-1-carboxamide (43.52 mg, 0.096 mmol, 65.4% yield). LCMS: 0.88 min, M+H 430.

4-(2-Acryloyl-1,2,3,4-tetrahydroisoquinolin-5-yl)-3-chloro-9H-carbazole-1-carboxamide (33 mg) was separated by chiral super-critical fluid chromatography (Chiral IC (3×25 cm, 5 μm); Mobile Phase: CO$_2$-MeOH 60-40 at 850 mL/min; sample preparation: 85 mg in 5 mL MeOH. The first peak eluting from the column provided one enantiomer of 4-(2-acryloyl-1,2,3,4-tetrahydroisoquinolin-5-yl)-3-chloro-9H-carbazole-1-carboxamide as a white powder (11.99 mg). $^1$H NMR (400 MHz, methanol-$d_4$) δ 8.11 (s, 1H), 7.59 (d, J=8.2 Hz, 1H), 7.52-7.41 (m, 2H), 7.39-7.28 (m, 1H), 7.26-7.13 (m, 1H), 6.89-6.79 (m, 1H), 6.74-6.50 (m, 2H), 6.32-6.10 (m, 1H), 5.88-5.62 (m, 1H), 4.95 (d, J=13.7 Hz, 2H), 3.83-3.54 (m, 2H), 2.66-2.49 (m, 1H), 2.37 (m, 1H). LCMS: 0.88 min, M+H 430. The second peak eluting from the column provided the other enantiomer of 4-(2-acryloyl-1,2,3,4-tetrahydroisoquinolin-5-yl)-3-chloro-9H-carbazole-1-carboxamide as a white powder (10.78 mg). $^1$H NMR (400 MHz, methanol-$d_4$) δ 8.11 (s, 1H), 7.59 (d, J=8.2 Hz, 1H), 7.52-7.41 (m, 2H), 7.38-7.29 (m, 1H), 7.24-7.16 (m, 1H), 6.90-6.79 (m, 1H), 6.73-6.52 (m, 2H), 6.32-6.13 (m, 1H), 5.86-5.64 (m, 1H), 4.97 (m, 2H), 3.82-3.55 (m, 2H), 2.58 (m, 1H), 2.44-2.27 (m, 1H). LCMS: 0.88 min, M+H 430.

The Examples in Table 1 were prepared by the general procedures described for Examples above or similar procedures known to those in the art, using the appropriate starting materials.

TABLE 1

| Example, Description | Structure | Name | Mass Spectrum |
|---|---|---|---|
| 25 (racemate) | 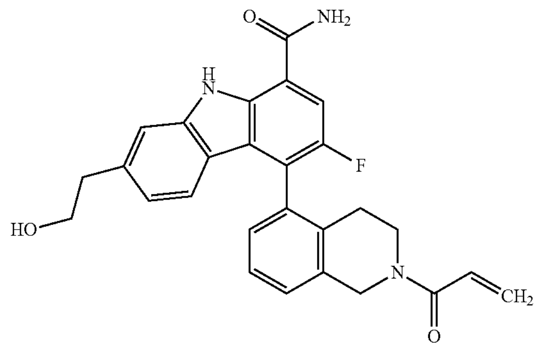 [SMILES: C=CC(=O)N1CCc2c(cccc2-c2c(F)cc(C(N)=O)c3[nH]c4cc(CCO)ccc4c23)C1] | 4-(2-acryloyl-1,2,3,4-tetrahydroisoquinolin-5-yl)-3-fluoro-7-(2-hydroxyethyl)-9H-carbazole-1-carboxamide | m/z 458 (M + H)+ |
| 26 (racemate) | 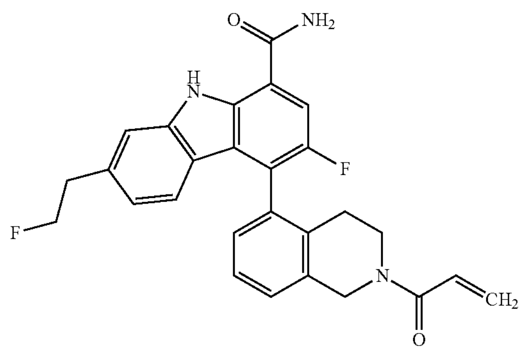 [SMILES: C=CC(=O)N1CCc2c(cccc2-c2c(F)cc(C(N)=O)c3[nH]c4cc(CCF)ccc4c23)C1] | 4-(2-acryloyl-1,2,3,4-tetrahydroisoquinolin-5-yl)-3-fluoro-7-(2-fluoroethyl)-9H-carbazole-1-carboxamide | m/z 460 (M + H)+ |
| 27 (racemate) | 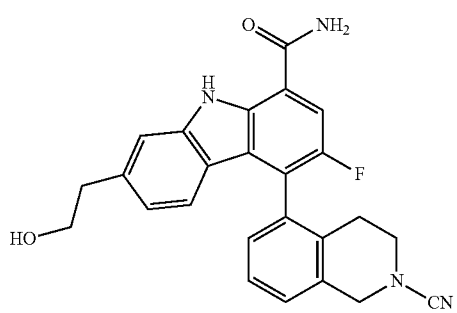 [SMILES: N#CN1CCc2c(cccc2-c2c(F)cc(C(N)=O)c3[nH]c4cc(CCO)ccc4c23)C1] | 4-(2-cyano-1,2,3,4-tetrahydroisoquinolin-5-yl)-3-fluoro-7-(2-hydroxyethyl)-9H-carbazole-1-carboxamide | m/z 429 (M + H)+ |
| 28 (racemate) | 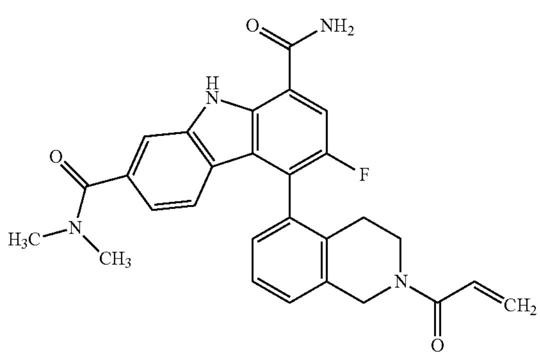 [SMILES: C=CC(=O)N1CCc2c(cccc2-c2c(F)cc(C(N)=O)c3[nH]c4cc(C(=O)N(C)C)ccc4c23)C1] | 4-(2-acryloyl-1,2,3,4-tetrahydroisoquinolin-5-yl)-3-fluoro-N7,N7-dimethyl-9H-carbazole-1,7-dicarboxamide | m/z 485 (M + H)+ |

TABLE 1-continued

| Example, Description | Structure | Name | Mass Spectrum |
|---|---|---|---|
| 29 (racemate) | 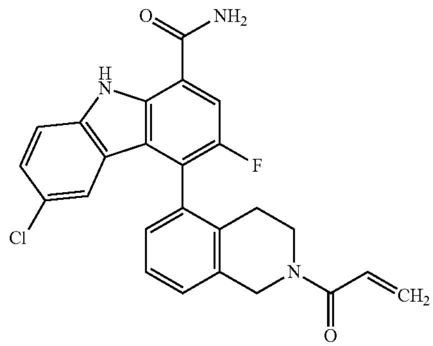 [SMILES: C=CC(=O)N1CCc2c(cccc2-c2c(F)cc(C(N)=O)c3[nH]c4ccc(Cl)cc4c23)C1] | 4-(2-acryloyl-1,2,3,4-tetrahydroisoquinolin-5-yl)-6-chloro-3-fluoro-9H-carbazole-1-carboxamide | m/z 448, 450 (M + H)+ |
| 30 (racemate) | 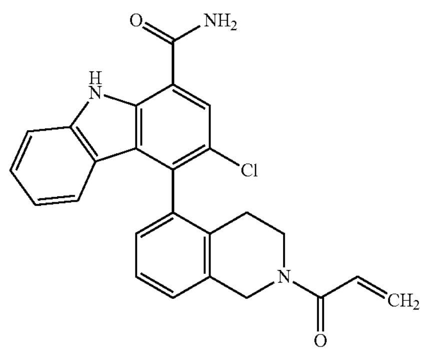 [SMILES: C=CC(=O)N1CCc2c(cccc2-c2c(Cl)cc(C(N)=O)c3[nH]c4ccccc4c23)C1] | 4-(2-acryloyl-1,2,3,4-tetrahydroisoquinolin-5-yl)-3-fluoro-9H-carbazole-1-carboxamide | m/z 430, 432 (M + H)+ |
| 31 (racemate) | 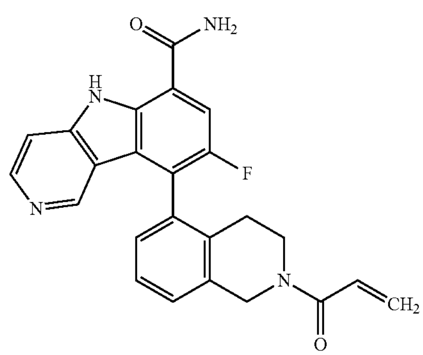 [SMILES: C=CC(=O)N1CCc2c(cccc2-c2c(F)cc(C(N)=O)c3[nH]c4ccncc4c23)C1] | 9-(2-acryloyl-1,2,3,4-tetrahydroisoquinolin-5-yl)-8-fluoro-5H-pyrido[4,3-b]indole-6-carboxamide | m/z 415 (M + H)+ |
| 32 (racemate) | 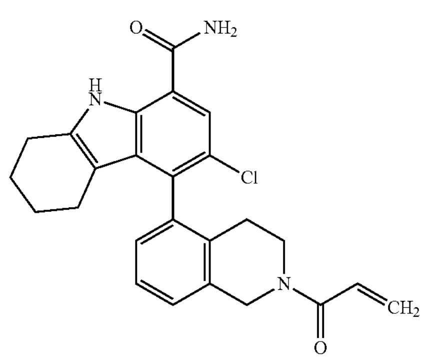 [SMILES: C=CC(=O)N1CCc2c(cccc2-c2c(Cl)cc(C(N)=O)c3[nH]c4c(c23)CCCC4)C1] | 5-(2-acryloyl-1,2,3,4-tetrahydroisoquinolin-5-yl)-6-chloro-2,3,4,9-tetrahydro-1H-carbazole-8-carboxamide | m/z 434, 436 (M + H)+ |

TABLE 1-continued

| Example, Description | Structure | Name | Mass Spectrum |
|---|---|---|---|
| 33 (racemate) | 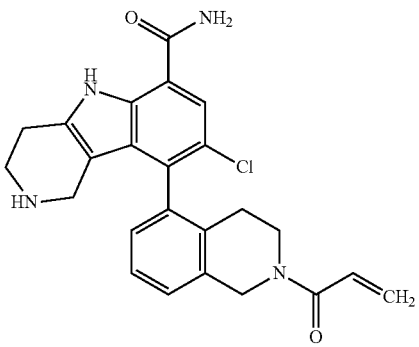 [SMILES: C=CC(=O)N1CCc2c(cccc2-c2c(Cl)cc(C(N)=O)c3[nH]c4c(c23)CNCC4)C1] | 9-(2-acryloyl-1,2,3,4-tetrahydroisoquinolin-5-yl)-8-chloro-2,3,4,5-tetrahydro-1H-pyrido[4,3-b]indole-6-carboxamide | m/z 435, 437 (M + H)+ |

Biological Assays

The pharmacological properties of the compounds of this invention may be confirmed by a number of biological assays. The exemplified biological assays, which follow, have been carried out with compounds of the invention.

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM MgCl$_2$, 0.015% Brij 35 surfactant and 4 mM DTT in 1.6% DMSO), with a final volume of 30 µL. After incubating at room temperature for 60 min, the reaction was terminated by adding 45 µL of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required for inhibiting 50% of kinase activity (IC$_{50}$). Compounds were dissolved at 10 mM in DMSO and evaluated at eleven concentrations.

Ramos FLIPR Assay

Ramos RA1 B cells (ATCC CRL-1596) at a density of 2×10$^6$ cells/mL in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, room temperature, 5 min) and resuspended at room temperature in RPMI minus phenol red with 50 mM HEPES and 10% FBS to a density of 1×10$^6$ cells/mL. 150 µL aliquots (150,000 cells/well) were plated into 96 well poly-D-lysine coated assay plates (BD 35 4640) and briefly centrifuged (Beckmann GS-CKR 800 rpm, 5 min, without brake). Next, 50 µL compound dilutions in 0.4% DMSO/RPMI minus phenol red+50 mM HEPES+10% FBS were added to the wells and the plate was incubated at room temperature in the dark for 1 hour. The assay plate was briefly centrifuged as above prior to measuring calcium levels. Using the FLIPRI (Molecular Devices), cells were stimulated by adding goat anti-human IgM (Invitrogen AHI0601) to 2.5 µg/mL. Changes in intracellular calcium concentrations were measured for 180 seconds and percent inhibition was determined relative to peak calcium levels seen in the presence of stimulation only. The Ramos assay measures the ability of a compound to move through the cell membrane into the cell interior. A lower IC$_{50}$ value indicates a greater ability to move into the cell interior.

Table 3 shows the Btk IC$_{50}$ values and the Ramos IC$_{50}$ values obtained from evaluation of Examples 1, 3, and 5-14 in the human recombinant Btk enzyme assay and in the Ramos FLIPR assay.

TABLE 3

| Example | Btk IC$_{50}$ value (nM) | Ramos IC$_{50}$ value (nM) |
|---|---|---|
| 1 | 0.18 | 25 |
| 3 | 0.075 | 4.6 |
| 5 | 0.067 | 2.4 |
| 6 | 0.12 | 23 |
| 7 | 0.18 | 10.7 |
| 8 | 0.077 | 6.9 |
| 9 | 0.045 | 2.3 |
| 10 | 0.30 | 22.2 |
| 11 | 0.13 | 16.3 |
| 12 | 0.37 | 6.2 |
| 13 | 0.13 | 9.2 |
| 14 | 0.073 | 7.8 |
| 24 | 0.18 | 3 |
| 25 | 1.5 | 28 |
| 26 | 0.029 | ND |
| 27 | 4.8 | 142 |
| 28 | 0.17 | 17 |
| 29 | 0.00026 | 107 |
| 30 | 0.0003 | 20 |
| 31 | 0.0003 | 13 |
| 32 | 0.0006 | 46 |
| 33 | 2.3 | ND |

Table 4 shows the Btk IC$_{50}$ values and the Ramos IC$_{50}$ values from the evaluation of Examples 5-12 and 14 and Comparative Examples 15 to 23 in the human recombinant Btk enzyme assay and the Ramos FLIPR assay.

TABLE 4

| Example | | | Comparative Example | | | Potency Difference | |
|---|---|---|---|---|---|---|---|
| Example Number | Btk[a] | Ramos[b] | Example Number | Btk[a] | Ramos[b] | Btk[c] | Ramos[d] |
| 5 | 0.067 | 2.4 | 15 | 4.0 | 72 | 60 | 30 |
| 6 | 0.12 | 23 | 16 | 4.5 | >300 | 38 | >13 |
| 7 | 0.18 | 11 | 17 | 14 | >300 | 78 | >27 |
| 8 | 0.077 | 6.9 | 18 | 1.5 | 65 | 19 | 9.4 |

TABLE 4-continued

| Example | | | Comparative Example | | | Potency Difference | |
|---|---|---|---|---|---|---|---|
| Example Number | Btk[a] | Ramos[b] | Example Number | Btk[a] | Ramos[b] | Btk[c] | Ramos[d] |
| 9 | 0.045 | 2.3 | 19 | 28 | >300 | 620 | >130 |
| 10 | 0.30 | 22 | 20 | 27 | >300 | 90 | >14 |
| 11 | 0.13 | 16 | 21 | 3.0 | >300 | 23 | >19 |
| 12 | 0.37 | 6.2 | 22 | 9.5 | 300 | 26 | 48 |
| 14 | 0.073 | 7.8 | 23 | 4.4 | 150 | 60 | 19 |

[a]$IC_{50}$ (nM) in the recombinant human Btk enzyme assay
[b]$IC_{50}$ (nM) in the Ramos FLIPR assay
[c]Ratio of $IC_{50}$ value in the recombinant human Btk enzyme assay for the Comparative Example to that for the corresponding Example.
[d]Ratio of $IC_{50}$ value in the Ramos FLIPR assay for the Comparative Example to that for the corresponding Example.

The compounds of Formula (I), as exemplified by Examples 5 to 12 and 14, have been compared to their stereoisomers, Comparative Examples 15 to 23, and have been found to have improved Btk potencies. Increased potency is indicated by a smaller Btk $IC_{50}$ value. As shown in Table 4, in the reported Btk assay, Examples 5 to 12 and 14 had Btk $IC_{50}$ values of less than 0.4 nM. In contrast, Comparative Examples 15 to 23 had Btk $IC_{50}$ values in the range of 1.5 to 28 nM. Comparisons of the Btk $IC_{50}$ values of Examples 5 to 12 and 14 to the Btk $IC_{50}$ values of their corresponding stereoisomers are also reported in Table 4. The Btk ratio is reported as the Btk $IC_{50}$ activity value of the corresponding stereoisomer (Comparative Examples 15 to 23) to the Btk $IC_{50}$ value for the Example of Formula (I). A higher Btk $IC_{50}$ ratio indicated improved potency for the Example compound compared to its comparative stereoisomer. The compounds of Formula (I), as exemplified by Examples 5 to 12 and 14, showed improved potencies of at least 19 times or greater, compared to their stereoisomers.

The compounds of Formula (I), as exemplified by Examples 5 to 12 and 14, have been compared to their stereoisomers, Comparative Examples 15-23, and have been found to have improved potencies in the Ramos FLIPR assay. Increased potency is indicated by a smaller Ramos $IC_{50}$ value. As shown in Table 4, in the reported Ramos assay, Examples 5 to 12 and 14 had Ramos $IC_{50}$ values of 23 nM or less. In contrast, Comparative Examples 15-23 had Ramos $IC_{50}$ values of 65 nM or greater. Comparisons of the Ramos $IC_{50}$ values of Examples 5 to 12 and 14 to the Ramos $IC_{50}$ values of their corresponding stereoisomers are also reported in Table 4. The Ramos ratio is reported as the Ramos $IC_{50}$ activity value of the corresponding stereoisomer (Comparative Examples 15-23) to the Ramos $IC_{50}$ value for the Example of Formula (I). A higher Ramos $IC_{50}$ ratio indicated improved potency for the Example compound compared to its stereoisomer. The compounds of Formula (I), as exemplified by Examples 5 to 12 and 14, showed improved Ramos potencies of at least 9.4 times or greater, compared to their stereoisomers.

The compounds of Formula (I), as exemplified by Examples 5 to 12 and 14, have been compared to their stereoisomers, Comparative Examples 15-23, and have been found to be advantageous. The compounds of Formula (I) have the surprising advantage of the combination of increased Btk potencies and increased Ramos activities, compared to their stereoisomers. Examples 5 to 12 and 14 showed a combination of improved Btk potencies of at least 19 times or greater, and improved Ramos potencies of at least 9.4 times or greater, compared to their stereoisomers.

These results indicate that the absolute three-dimensional arrangement of the molecule is important for the potency of the compound of Formula (I).

Human Recombinant Btk Dissociation Dialysis Assay

A test compound was incubated with human recombinant Btk (100 nM) for 1.5 h at a concentration of 25 times the $IC_{50}$ of Btk inhibition or 200 nM (whichever was greater). The incubation was performed in assay buffer (20 mM HEPES pH 7.5, 10 mM $MgCl_2$, 2 mM dithiothreitol, 50 μg/mL bovine serum albumen and 0.015% Brij 35). The reaction mixture was then dialyzed twice for 6 h each time against 1 L of assay buffer. The dialyzed reaction mixture (0.5 μL) was then diluted into a solution (100 μL) of ATP (2 mM) and substrate peptide (5 μM Src-tide, AnaSpec) such that the final Btk concentration was 1 nM (along with any inhibitor still bound). The assay was performed in matrix polypropylene 384-well plates. The reaction progress curve was monitored on the Caliper LABCHIP® by electrophoretic separation of the substrate and phosphorylated product (pressure −1.2 psi, downstream voltage −500 V, upstream voltage −2300 V). Reaction velocity was measured over the linear phase and percent recovery of Btk activity was assessed at 2 h by comparing the fraction of phosphorylated peptide product relative to a DMSO-treated Btk control reaction containing no Example inhibitor. A control reaction with no Btk was also used to measure the background signal. A reversible inhibitor would show nearly complete recovery of Btk activity, while an irreversible inhibitor, would show little or no recovery of Btk activity.

The invention claimed is:

1. A compound of Formula (I)

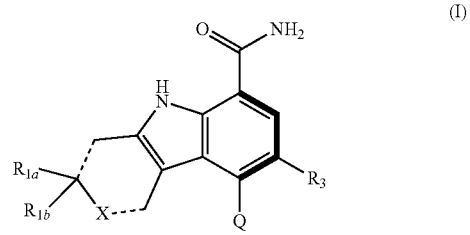

or a salt thereof, wherein:

the two dotted lines represent either two single or two double bonds; and $R_{1b}$ is present only if said two dotted lines are two single bonds;

X is:
(i) $CR_{2a}R_{2b}$ or $NR_{2b}$ when the two dotted lines represent two single bonds; or
(ii) $CR_{2a}$ or N when the two dotted lines represent two double bonds;

Q is:

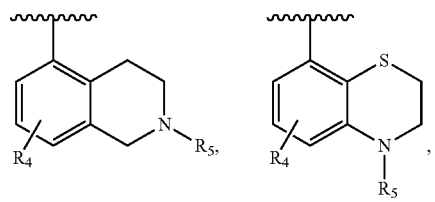

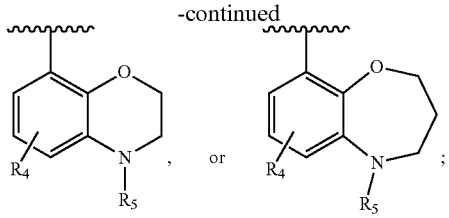

R$_{1a}$ is H, —CN, —CF$_3$, —CH$_3$, —CR$_{6a}$R$_{6b}$OH, —CH$_2$CH$_2$OH, —CH(OH)CH$_2$OH, —CH$_2$CH$_2$F, —NHR$_7$, or —C(O)NR$_{8a}$R$_{8b}$;

R$_{1b}$, when present, is H or —CH$_3$, provided that if R$_{1a}$ is H, then R$_{1b}$ is also H;

R$_{2a}$ is H, F, or Cl, provided that if R$_{1a}$ is other than H, then R$_{2a}$ is H;

R$_{2b}$, when present, is the same as R$_{2a}$;

R$_3$ is F, Cl, —CN, or —CH$_3$;

R$_4$ is H, F, Cl, —OCH$_3$, or —OCF$_3$;

R$_5$ is —CN or —C(O)CH=CH$_2$;

R$_{6a}$ and R$_{6b}$ are independently H or —CH$_3$;

R$_7$ is C$_{1-4}$ alkyl; and

R$_{8a}$ and R$_{8b}$ are independently H or —CH$_3$.

2. The compound according to claim 1 or a salt thereof, wherein:

Q is:

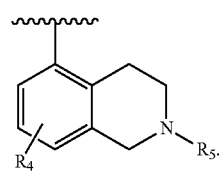

3. The compound according to claim 1 or a salt thereof, wherein:

Q is:

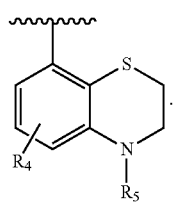

4. The compound according to claim 1 or a salt thereof, wherein:

Q is:

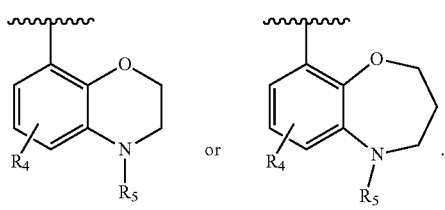

5. The compound according to claim 1 or a salt thereof, wherein:

X is:

(i) CR$_{2a}$R$_{2b}$ when the two dotted lines represent two single bonds; or (ii) CR$_{2a}$ when the two dotted lines represent two double bonds.

6. The compound according to claim 1 or a salt thereof, wherein:

X is:

(i) NR$_{2b}$ when the two dotted lines represent two single bonds; or (ii) N when the two dotted lines represent two double bonds.

7. The compound according to claim 1 or a salt thereof, wherein:

R$_{1a}$ is H, —CF$_3$, or —C(CH$_3$)$_2$OH;

R$_{1b}$ is H;

R$_{2a}$ is H or F, provided that if R$_{1a}$ is other than H, then R$_{2a}$ is H;

R$_{2b}$, when present, is the same as R$_{2a}$;

R$_3$ is F, Cl, or —CH$_3$; and

R$_4$ is H.

8. The compound according to claim 1 or a salt thereof, wherein:

R$_{1a}$ is H, —CF$_3$, or —C(CH$_3$)$_2$OH;

R$_{1b}$ is H;

R$_{2a}$ is H or F, provided that if R$_{1a}$ is other than H, then R$_{2a}$ is H;

R$_{2b}$, when present, is the same as R$_{2a}$;

R$_3$ is F or Cl; and

R$_4$ is H.

9. The compound according to claim 1 or a salt thereof, wherein:

R$_{1a}$ is H, —CF$_3$, or —C(CH$_3$)$_2$OH;

R$_{1b}$ is H;

R$_{2a}$ is H or F, provided that if R$_{1a}$ is other than H, then R$_{2a}$ is H;

R$_{2b}$, when present, is the same as R$_{2a}$;

R$_3$ is F; and

R$_4$ is H.

10. The compound according to claim 1 or a salt thereof, wherein said compound has the structure of Formula (Ia):

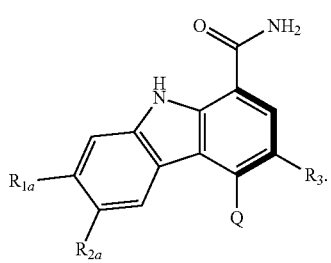

11. The compound according to claim 1 or a salt thereof, wherein said compound has the structure of Formula (Ib):

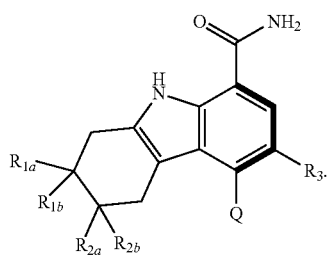

(Ib)

12. The compound according to claim 1 or a salt thereof, wherein said compound is:
   4-(2-acryloyl-1,2,3,4-tetrahydroisoquinolin-5-yl)-3-fluoro-9H-carbazole-1-carboxamide, single enantiomer (5);
   5-(2-acryloyl-1,2,3,4-tetrahydroisoquinolin-5-yl)-3,3,6-trifluoro-2,3,4,9-tetrahydro-1H-carbazole-8-carboxamide, single enantiomer (6);
   4-(2-acryloyl-1,2,3,4-tetrahydroisoquinolin-5-yl)-3-fluoro-7-(trifluoromethyl)-9H-carbazole-1-carboxamide, single enantiomer (7);
   4-(4-acryloyl-3,4-dihydro-2H-benzo[b][1,4]oxazin-8-yl)-3-fluoro-9H-carbazole-1-carboxamide, single enantiomer (8);
   5-(2-acryloyl-1,2,3,4-tetrahydroisoquinolin-5-yl)-6-fluoro-2-(S)-(2-hydroxypropan-2-yl)-2,3,4,9-tetrahydro-1H-carbazole-8-carboxamide, single diastereomer (9);
   5-(2-acryloyl-1,2,3,4-tetrahydroisoquinolin-5-yl)-6-fluoro-2-(trifluoromethyl)-2,3,4,9-tetrahydro-1H-carbazole-8-carboxamide, single homochiral diastereomers (10 and 11);
   4-(5-acryloyl-2,3,4,5-tetrahydrobenzo[b][1,4]oxazepin-9-yl)-3-fluoro-7-(trifluoromethyl)-9H-carbazole-1-carboxamide, single enantiomeric atropisomer (12);
   4-(4-acryloyl-3,4-dihydro-2H-benzo[b][1,4]thiazin-8-yl)-3-fluoro-9H-carbazole-1-carboxamide, single enantiomer (14); or
   4-(2-acryloyl-1,2,3,4-tetrahydroisoquinolin-5-yl)-3-chloro-9H-carbazole-1-carboxamide (24).

13. A pharmaceutical composition comprising a compound according to claim 1 and a pharmaceutically acceptable carrier.

* * * * *